United States Patent
Anderson et al.

(10) Patent No.: US 7,749,155 B1
(45) Date of Patent: Jul. 6, 2010

(54) DIGITAL SOUND RELAXATION AND SLEEP-INDUCING SYSTEM AND METHOD

(75) Inventors: Troy Gene Anderson, Marblehead, MA (US); Kevin Bailey, Ottawa (CA); Jeffrey D. Thompson, Encinitas, CA (US); Rudy Anthony Vandenbelt, Ottawa (CA)

(73) Assignee: Headwaters R+D Inc., Ottawa (CA)

( * ) Notice: Subject to any disclaimer, the term of this patent is extended or adjusted under 35 U.S.C. 154(b) by 0 days.

(21) Appl. No.: 09/159,520

(22) Filed: Sep. 23, 1998

Related U.S. Application Data

(63) Continuation-in-part of application No. 08/706,136, filed on Aug. 30, 1996, which is a continuation-in-part of application No. 08/706,134, filed on Aug. 30, 1996, now Pat. No. 5,867,580.

(51) Int. Cl.
*A61M 21/00* (2006.01)
*A61F 2/00* (2006.01)
*A61B 5/00* (2006.01)
*G06F 17/00* (2006.01)

(52) U.S. Cl. .............................. 600/28; 600/26; 600/27; 600/29; 600/300; 700/94

(58) Field of Classification Search ............. 600/26–29, 600/300; 700/94; 128/897, 898
See application file for complete search history.

(56) References Cited

U.S. PATENT DOCUMENTS 2,304,095 A    12/1942    Hull (Continued)

FOREIGN PATENT DOCUMENTS

WO    WO 98/09373    3/1998

OTHER PUBLICATIONS

A Pilot Study Of EEG Entrainment As a Sleep Aid, by Clinton et al., appearing at Abstracts, Associated Professional Sleep Societies, 11th Annual Meeting (San Francisco: Jun. 10-15, 1997).

(Continued)

*Primary Examiner*—Devona E Faulk
(74) *Attorney, Agent, or Firm*—Albert Peter Durigon

(57) ABSTRACT

In one embodiment, an improved-customizability digital sound relaxation system having a sound card receiving port and a collectable sound card are cooperative to play prerecorded natural or other sounds by depressing one of a plurality of sound selector switches and a sound card selector switch. The new sounds of each collectable sound card customize the library of available sounds to individual taste. In another embodiment, an improved-flexibility digital sound relaxation system having at least two (2) prerecorded sounds stored at first and second memory locations of internal or external/internal memory devices may be selected and combined for concurrent and/or individual replay by depressing one of a plurality of sound selector switches and a combine switch, or by depressing one of a plurality of sound selector switches, a sound card selector switch and a combine switch. In this manner, from eighteen (18) digitally prerecorded sounds of the preferred embodiment ninety (90) individually selectable and/or combinable sounds are made available. In either embodiment, natural or other sounds may be stored in loop or sound bite format in either or both of the internal and external memories. In a further sound relaxation and sleep-inducing embodiment, first and second preselected sound patterns selected respectively to mask sound and soothe the listener and to induce a state of deep relaxation that helps the listener to fall asleep may be selected by depressing combination mode select and sequential sound selector switches. In alarm mode, sound select and alarm check buttons respectively allow any sound of the library of prerecorded sounds (sound card or internal, single or mixed) to be selected as the alarm wake-up sound and one-touch alarm status display and audible alarm replay of any sound selected at wake-up volume in sound wake-up mode.

3 Claims, 16 Drawing Sheets

U.S. PATENT DOCUMENTS

| | | | |
|---|---|---|---|
| 2,711,165 A | 6/1955 | Leavenworth | |
| 3,160,159 A | 12/1964 | Hoody et al. | |
| 3,384,074 A | 5/1968 | Rautiola et al. | |
| 3,576,185 A | 4/1971 | Schulz et al. | |
| 3,712,292 A | 1/1973 | Zentmeyer, Jr. | |
| 3,753,433 A | 8/1973 | Bakerich et al. | |
| 3,826,243 A | 7/1974 | Anderson | |
| 3,837,331 A | 9/1974 | Ross | |
| 3,884,218 A | 5/1975 | Monroe | |
| 4,034,741 A | 7/1977 | Adams et al. | |
| 4,141,344 A | 2/1979 | Barbara | |
| 4,227,516 A | 10/1980 | Meland et al. | |
| 4,573,449 A | 3/1986 | Warnke | |
| 4,589,779 A * | 5/1986 | Hatta et al. | 368/74 |
| 4,834,701 A | 5/1989 | Masaki | |
| 5,036,858 A | 8/1991 | Carter et al. | |
| 5,163,426 A | 11/1992 | Czeisler et al. | |
| 5,167,228 A | 12/1992 | Czeisler et al. | |
| 5,176,133 A | 1/1993 | Czeisler et al. | |
| 5,213,562 A | 5/1993 | Monroe | |
| 5,305,423 A | 4/1994 | Clynes | |
| 5,352,181 A * | 10/1994 | Davis | 600/28 |
| 5,356,368 A | 10/1994 | Monroe | |
| 5,619,179 A | 4/1997 | Smith | 340/384.72 |
| 5,633,985 A | 5/1997 | Severson et al. | |

OTHER PUBLICATIONS

Product advertisement for stress relief CD entitled "Natural Stress Relief," undated.
Product advertisement for stress relief CD entitled "Delta Sync Sleep System," undated.
Product advertisement for stress relief CD entitled "DE-STRESS," undated.
Product advertisement for sound card, entitled "Sleep Enhancers," undated.
Marsona 1250, product brochure, author unknown, 1992.

* cited by examiner

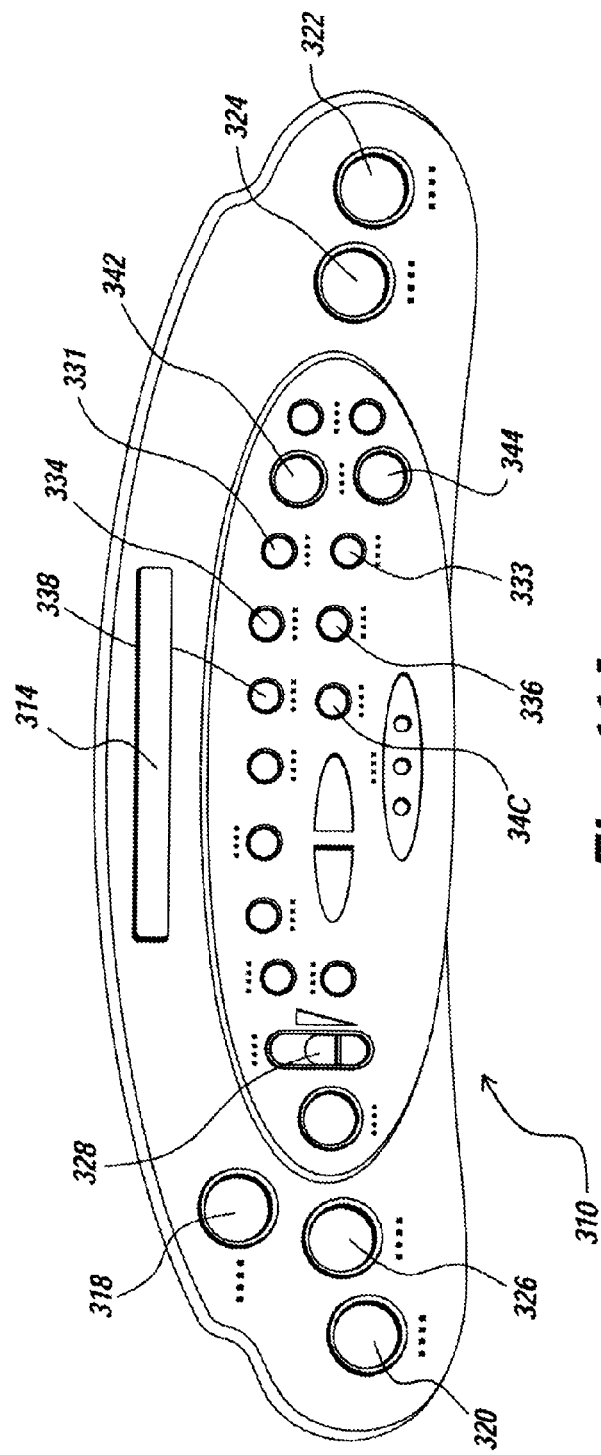

| | | Ocean Surf 43.7 | | Stream 16.9 | | Rain 10.8 | | White Noise 11 | | Woodlands 45.4 | | Wind 20.4 | |
|---|---|---|---|---|---|---|---|---|---|---|---|---|---|
| 1 | 9260 | 7 | 6.86 | 18 | 17.73 | 28 | 27.90 | 27 | 27.27 | 7 | 6.60 | 15 | 14.71 |
| 2 | 8929 | 1 | 1.42 | 4 | 3.68 | 6 | 5.79 | 6 | 5.66 | 1 | 1.37 | 3 | 3.05 |
| 3 | 8620 | 1 | 1.47 | 4 | 3.81 | 6 | 5.99 | 6 | 5.86 | 1 | 1.42 | 3 | 3.16 |
| 4 | 8333 | 2 | 1.52 | 4 | 3.94 | 6 | 6.20 | 6 | 6.06 | 1 | 1.47 | 3 | 3.27 |
| 5 | 8065 | 2 | 1.57 | 4 | 4.07 | 6 | 6.41 | 6 | 6.26 | 2 | 1.52 | 3 | 3.38 |
| 6 | 7692 | 2 | 1.65 | 4 | 4.27 | 7 | 6.72 | 7 | 6.57 | 2 | 1.59 | 4 | 3.54 |
| 7 | 7463 | 2 | 1.70 | 4 | 4.40 | 7 | 6.92 | 7 | 6.77 | 2 | 1.64 | 4 | 3.65 |
| 8 | 7143 | 2 | 1.78 | 5 | 4.60 | 7 | 7.23 | 7 | 7.07 | 2 | 1.71 | 4 | 3.81 |
| 9 | 6849 | 2 | 1.85 | 5 | 4.79 | 8 | 7.54 | 7 | 7.37 | 2 | 1.79 | 4 | 3.98 |
| 10 | 6579 | 2 | 1.93 | 5 | 4.99 | 8 | 7.85 | 8 | 7.68 | 2 | 1.86 | 4 | 4.14 |
| 11 | 6250 | 2 | 2.03 | 5 | 5.25 | 8 | 8.27 | 8 | 8.08 | 2 | 1.96 | 4 | 4.36 |
| 12 | 5952 | 2 | 2.13 | 6 | 5.52 | 9 | 8.68 | 8 | 8.49 | 2 | 2.05 | 5 | 4.58 |
| 13 | 5618 | 2 | 2.26 | 6 | 5.84 | 9 | 9.20 | 9 | 8.99 | 2 | 2.18 | 5 | 4.85 |

*Fig. 14*

DIGITAL SOUND RELAXATION AND SLEEP-INDUCING SYSTEM AND METHOD

CROSS-REFERENCE TO RELATED APPLICATIONS

This is a continuation-in-part of co-pending United States utility patent applications entitled Improved-Customizability Digital Sound Relaxation System, Ser. No. 08/706,136, and Improved-Flexibility Digital Sound Relaxation System, Ser. No. 08/706,134 now U.S. Pat. No. 5,867,580, each filed on Aug. 30, 1996, and each incorporated herein by reference.

FIELD OF THE INVENTION

This invention is drawn to the field of audio components, and more particularly, to a digital sound relaxation and sleep-inducing system and method.

BACKGROUND OF THE INVENTION

It is known that naturally recurring sounds of nature, like rainfall or the rolling of the ocean surf, possess the power to calm and sooth. Various techniques that have simulated these natural sounds in the home or office, both to reproduce their calming and soothing effect and to mask unwanted noise, have often resulted in improved mental concentration and enhanced relaxation.

LP's, CD's or audio cassettes belong to one class of devices that have been employed to reproduce such natural or other sounds in the home or office.

For this class of devices, preselected natural sounds are recorded on the LP's, CD's or audio cassettes and replayed on the corresponding sound reproduction equipment, such as a record player, CD player or tape deck.

Although these media offer the advantage of comparatively-long intervals of continuous, non-repetitive replay, they are subject to a potentially annoying and disruptive repeat/rewind cycle, can be cumbersome to use and are subject to wear and tear over their useful life.

When the record needs to be turned over, or when the audio cassette continuous replay mechanism resets itself, or when the CD player, following its replay program, stops to reposition its read laser, such devices exhibit a quite pronounced disruption of the natural sound being reproduced thereby, which may impair its intended calming and soothing effects. In addition, any background noise is unmasked during the repeat cycle, which likewise may adversely impact the intended calming and soothing effects of the natural sound being replayed.

The collectability of the CD's, LP'S and audio cassettes of this class of devices offers individuals the advantage to customize their library of prerecorded natural sounds according to individual taste. However, the separate purchase of another LP, CD or audio cassette is typically required for each and every different sound to be collected.

Another class of devices for playing prerecorded natural or other sounds in the home or office is represented by the so-called digital sound soother, or sound conditioner, devices. For this class of devices, any one of a plurality of natural sounds prerecorded in internal digital memory (ROM) is selected for replay by the touch of a control button. In the Tranquil Moments™ TM-500 Sound Relaxation System commercially available from the Brookstone, Inc. Company, six (6) natural and other sounds are digitally recorded (Ocean, Stream, Rain, Waterfall, Summer Night and Soother sounds), and in the Marsona® 1250 Sound Conditioner, ten (10) natural sounds (Surf; Surf with random overlay of Sea Gulls & Bell Buoy at random times; Surf "2"; Rain Downpour; Rain Shower; Rain Shower with random overlay of Evening Bird Songs at random times; Waterfall; Crickets and Spring Peepers randomly overlaid on Rain, and Babbling Brook sounds) are prerecorded therein. The Marsona® 1250 Sound Conditioner is commercially available from the Marpac Corporation.

In the Digital Sound Soother XS, commercially available from Sharper Image, Inc., three (3) types of continuous sounds are available for selection, a Harbor sound with Waves and Gulls, a Countryside sound with Crickets and Frogs, and a White Noise sound. To the continuous Harbor sound, auxiliary Fog Horn, Seal and Ships Bell sounds may be randomly overlayed by an auxiliary sounds volume control slide, and to the continuous Countryside sound, auxiliary Dove, Owl, Wolf and Loons sounds may be randomly overlayed by the volume slide.

The utility of the heretofore known sound soother, or sound conditioner, devices, however, has been limited by their lack of customizability and by their inflexibility.

The heretofore known devices have been inflexible, in that the only choice of sounds presented to individuals has been limited to the selection of the particular prerecorded natural sounds digitally stored therein. For the Tranquil Moments™ TM-500 Sound Relaxation System, for example, one, and only one, of the Ocean, Stream, Rain, Waterfall, Summer Night and Soother sounds may be selected for replay by depressing a corresponding sound selector button. The Marsona® 1250 Sound Conditioner device, also only allows one, and only one, of the sounds prerecorded therein to be selected for replay by depressing a corresponding sound selector button. For the Digital Sound Soother XS device, the volume slide only controls the volume (from "off" to full volume) of the auxiliary sounds that are overlaid on the continuous sounds thereof.

The heretofore known sound soother, or sound conditioner, devices have suffered from a lack of customizability, in that individuals who for any reason desire a natural sound not prerecorded in the internal digital memory of the heretofore known devices have had no choice but to acquire another such device that does have the desired natural sound prerecorded therein. Not only has this resulted in frustration if no such device were available, but has required another cash outlay for the other sound soother device that contained the desired sound.

SUMMARY OF THE INVENTION

It is a principal object of the present invention to provide a digital sound relaxation and sleep-inducing system and method.

It is a related object to provide a digital sound relaxation and sleep-inducing system and method that not only masks noise and soothes the listener helping the listener to relax, but also induces a state of deep relaxation to help the listener fall asleep.

It is another object to provide a digital sound relaxation and sleep-inducing system that effectively integrates alarm and alarm check functions with sound select functions to provide selectable wake-up sounds customized to individual taste and to provide "one-touch" alarm parameter audible and visual display.

It is a further object of the present invention to provide a digital sound relaxation and sleep-inducing system and method that may be implemented at reasonable cost making both the relaxation and the sleep-inducing benefits derived therefrom available to individuals of the mass market.

In accord therewith, the present invention discloses a digital sound relaxation and sleep-inducing system that includes a housing; speakers mounted to the housing; at least one selector switch; a display; at least one digital memory storing samples of prerecorded sounds; and a processor-implemented sound controller, that is mounted to the housing, connected to the speakers, the at least one selector switch, the display and to the at least one digital memory, and is selectably operable in a sound relaxation mode, a sound relaxation and sleep-inducing mode, and in an alarm mode.

In said sound relaxation mode, the processor-implemented sound controller is operative to replay the sample of the prerecorded sound selected in accord with a first preselected sound pattern selected to mask noise, soothe the listener, and help her to relax, and in the sound relaxation and sleep-inducing mode, the processor-implemented sound controller is operative to replay the sample of the sound selected in accord with a second preselected sound pattern, different from said first sound pattern, selected to synergistically co-act with the listener's biorhythms to induce a state of deep relaxation that helps the listener to fall asleep. In the presently preferred embodiment, the first preselected sound pattern repetitively replays the sample of the prerecorded sound selected at its record (sampling) rate continuously and without disrupting pauses, and the second preselected sound pattern repetitively replays the sample of the prerecorded sound selected at progressively slower replay rates in successive time intervals. In the preferred embodiment, the progressively slower play-back in successive time intervals of the second preselected sound pattern is implemented by replaying the sample of the prerecorded sound selected the whole number of times the sample duration is contained in each successive time interval at each progressively slower playback rate. Other first and second sound patterns, and other ways of implementing the second preselected sound pattern of the presently preferred embodiment, may be employed without departing from the inventive concepts.

In one alarm mode, the processor-implemented sound controller is operative in alarm set mode to identify any prerecorded sound in said memory as an alarm wake-up sound and to replay that sound as the alarm wake-up sound. The listener in this manner may customize the alarm wake-up sound to individual preference.

In another alarm mode, the processor-implemented sound controller is operative in one-touch alarm check mode to display alarm status and to replay any prerecorded sound selected as an alarm wake-up sound. In this way, the listener is provided with a visible indication of alarm status and mode parameters and an audible replay of a selected wake-up sound at wake-up volume in sound wake-up mode.

BRIEF DESCRIPTION OF THE DRAWINGS

Other objects, advantageous features and inventive aspects of the present invention will become apparent as the invention becomes better understood by referring to the following detailed description of the presently preferred embodiments, and to the drawings, wherein:

FIG. 14 is a table useful in explaining the presently preferred implementation of the second preselected sound pattern of the digital sound relaxation and sleep-inducing system and method in accord with the present invention.

DETAILED DESCRIPTION OF THE PREFERRED EMBODIMENTS

The term digital sound relaxation system as used herein denotes any device having (1) one or more operator input devices for allowing selection of individual ones of a plurality of prerecorded natural (and/or other) sounds, (2) a digital memory in which are stored the plurality of prerecorded natural or other sounds to be selected by the one or more operator input devices and (3) a digital controller responsive to one or more operator input selections to replay the selected one of the plurality of prerecorded sounds.

As used herein, the term collectable sound card means any device having (1) a digital memory in which a plurality of natural or other sounds are stored in a predetermined format and (2) a connector member for connection with a digital sound relaxation system.

Figure 1A:
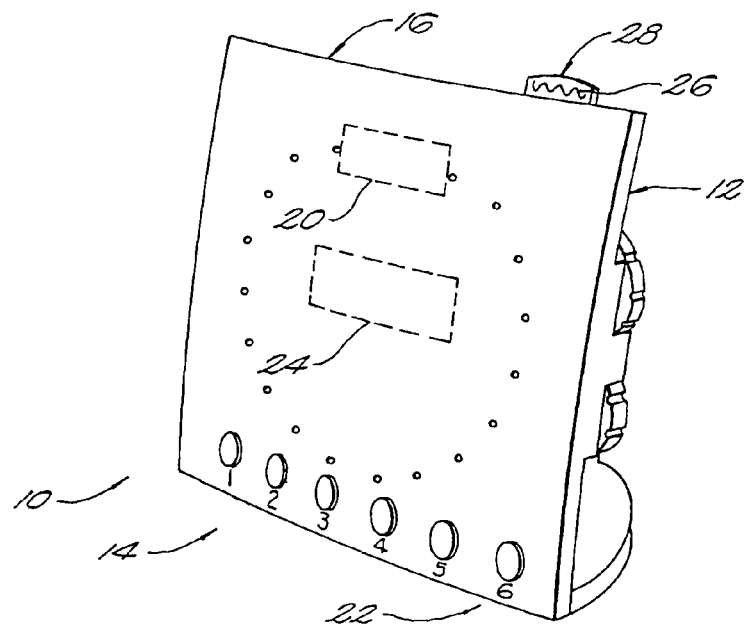
FIG. 1 illustrates in the FIGS. 1A, 1B thereof front and rear perspective views of one embodiment of an improved sound relaxation system in accord with the present invention providing individuals the capability to customize their library of natural sounds.
Figure 1B:
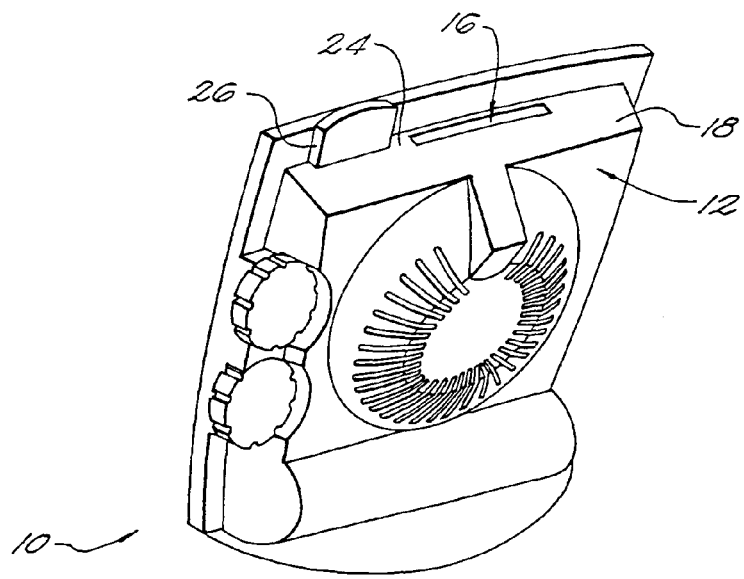

Referring now to FIGS. 1A, 1B, generally designated at 10 are front and rear perspective views of one presently preferred embodiment of an improved digital sound relaxation system in accord with the present invention. The device 10 of the invention provides individuals the capability to customize their library of natural sounds, by adding sounds contained in a collectable sound card to be described.

The improved system 10 includes a housing generally designated 12 and a plurality of sound selector switches generally designated 14. The switches 14 are arranged in laterally spaced apart relation proximate the bottom edge of the housing 12. Although six (6) individual selector switches 14 are presently preferred, any input device or devices for allowing selection of individual ones of a plurality of prerecorded natural sounds to be described may be employed in accord with the present invention.

A collectable sound card receiving port generally designated 16 is provided through the top wall 18 of the housing 12. Although it is preferred to locate the port 16 through the top wall 18 of the housing 12, any other collectable sound card receiving interface that is user-friendly, and easy-to-access, may be employed in accord with the present invention.

An electrical connector schematically illustrated in dashed outline 20 is provided in the port 16 of the housing 12. The electrical connector 20 is adapted to mate with the electrical connector to be described of a collectable sound card.

Figure 2:
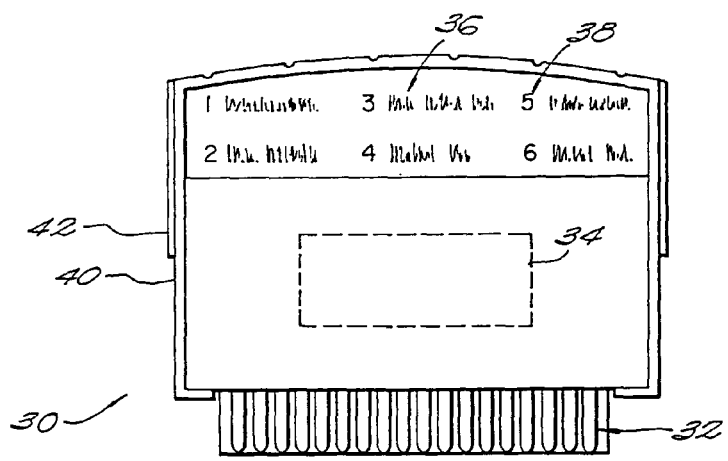
FIG. 2 is a front elevational view of a collectable sound card for a digital sound relaxation system in accord with the present invention.

Referring now briefly to FIG. 2, generally designated at 30 is a front elevational view of a collectable sound card in accord with the present invention. An electrical connector generally designated 32 is provided at the bottom end thereof. The collectable sound card 30 is slidably received within the port 16 (FIG. 1) of the housing 12 (FIG. 1), in such a way that the connector 32 of the collectable sound card 30 mates with the electrical connector 20 (FIG. 1) provided therefor in the sound card receiving port 16 (FIG. 1).

The collectable sound card 30 includes a digital memory illustrated in dashed outline 34 in which are stored, in a manner to be described, a plurality of preselected natural or other sounds. In the presently preferred embodiments, memory 34 includes four (4) megabytes of RAM memory in which six (6) prerecorded sounds are digitally stored, although a different memory size, and a different number of prerecorded sounds, may be employed in accord with the present invention.

The collectable sound card 30 bears first indicia schematically illustrated by "wavy lines" generally designated 36, that names or otherwise identifies each of the particular natural sounds prerecorded in its digital memory 34, and bears second whole number indicia generally designated 38, that enumerates the prerecorded natural sounds of its memory 34. The whole number indicia 38 correspond to whole number indicia generally designated 22 (FIG. 1) provided proximate to each of the sound selector switches 14 (FIG. 1) along the bottom edge of the housing 12 (FIG. 1). Although the corresponding indicia 22, 38 on the collectable sound card 30 and proximate the switches 14 (FIG. 1) of the device 10 (FIG. 1) are in the form of the whole numbers from one (1) to six (6), other indicia may be employed to correlate or associate each prerecorded natural sound identified by the indicia 36 with another switch 14 (FIG. 1) in accord with the present invention. Indicia, not shown, may be provided on the rear of the collectable sound card 30 that names, as a whole, the particular collection of natural (and/or other) sounds contained on each collectable sound card 30.

Travel-limiting shoulders 42 are preferably provided on the side walls 40 of the collectable sound card 30. The travel-limiting shoulders 42 abut walls 24 (FIG. 1) of the port 16 (FIG. 1), when it is slidably received therewithin, thereby seating the same in the device 10 (FIG. 1). The collectable sound card 30 is preferably provided on its back face with a contour, not shown, that conforms to the thumb of a user, and arcuate ribs, not shown, are provided, in spaced-apart relation in the contour to fractionally grip the thumb when received therewithin.

Returning now to FIG. 1, the device 10 includes an internal digital memory schematically illustrated in dashed line 24 in which a plurality of prerecorded natural or other sounds are digitally stored in a manner to be described.

A two-position selector switch 26 is slidably mounted to the top wall 18 of the housing 12. In the "off" position, not shown, of the two-position selector switch 26, the switch is recessed lower within the housing 12, while in its illustrated "on" position, the head of the switch 26 appears above the top wall 18 of the device 12. In the "on" position of the selector switch 26, indicia schematically illustrated by "wavy lines" generally designated 28 appear above the top wall 18 of the device 10 to indicate that the collectable sound card receiving port 16 has been activated.

As appears more fully below, in the "off" position of the selector switch 26, depressing any one of the switches 14 selects another one of the prerecorded natural sounds stored in the memory 24 for replay, while in the "on" position of the selector switch 26, depressing any one of the switches 14 selects another one of the prerecorded natural sounds stored in the external memory 34 (FIG. 2) of the collectable sound card for replay The correlative indicia 22, 38 (FIGS. 1 and 2, respectively) indicate which sounds, as indicated by indicia 36 (FIG. 2), of the collectable sound card correspond to which sound selector switches of 14 of the device 10. In this manner, the same sound selector switches 14 are enabled to select among the plurality of prerecorded natural sounds contained either in the internal memory 24 of the device 10 or in the external memory 34 (FIG. 2) of each collectable sound card.

The device 10 includes an on/off rotary switch, a four (4)-position interval selector switch and a pause/resume button. These switches form no part of the present invention and are not further described herein.

The prerecorded natural sounds may be digitally stored in internal and/or external digital memory in one of a loop format and a sound bite format. In general, the loop format is preferred for continuous-type natural and/or other sounds, such as an ongoing Rain sound or an always-surging Brook sound, while the sound bite format is preferred for sporadic-type natural and/or other sounds, such as Sea Gulls or Thunder sounds.

Figure 3A:
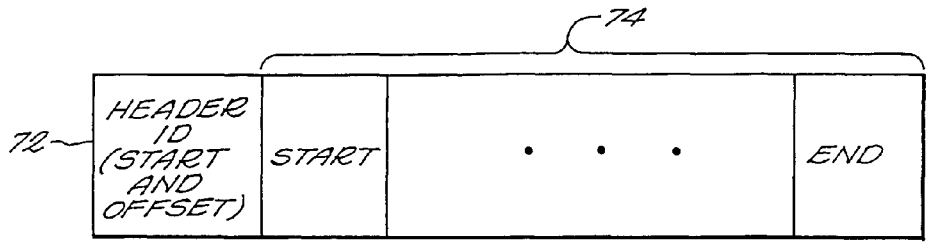
FIG. 3 illustrates in the FIGS. 3A, 3B thereof diagrams respectively representing loop format and sound bite format data structures in accord with the present invention.

Referring now to FIG. 3A, generally designated at 70 is a diagram illustrating a loop format data structure. The loop format data structure 70 includes a header 72. The header 72 identifies itself as "loop format" and identifies the length of the data record stored in loop format. As schematically shown by a bracket 74, the loop format defines (1) a plurality of addressable memory locations and (2) start and end locations, such that a different part of the same natural (or other) sound is digitally stored at another address location and in such a way that the parts digitally stored at the start and end locations are as acoustically-seamless as possible. A processor-implemented loop format subroutine to be described is called whenever a header identifies itself as loop format for replaying each at least one prerecorded natural (or other) sound digitally stored in loop format. In the presently preferred embodiments, each prerecorded natural sound stored in loop format is allocated approximately two-thirds (0.66) MB of memory, which has been found to provide minimalized perception of sound repetition during playback.

Figure 3B:
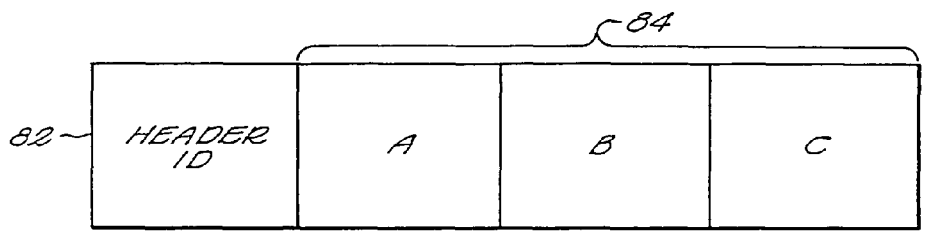

Referring now to FIG. 3B, generally designated at 80 is a diagram illustrating a sound bite type format data structure in accord with the present invention. The sound bite type format data structure 80 is particularly well suited for sporadic-type natural sounds, providing natural sounding (free of perceived repetition) sound reproduction with a minimum usage of digital memory space. The sound bite format data structure 80 includes a header portion 82. The header 82 identifies itself as a sound bite type format data structure and identifies the locations and lengths of three (3) data records. As shown by a bracket 84, the sound bite format defines three (3) pluralities of addressable memory locations designated "A", "B", and "C," such that another self-contained and complete-in-itself version of the same natural (or other) sound is digitally stored in each of said three (3) pluralities of addressable memory locations. A processor-implemented sound bite format subroutine to be described is called whenever a header identifies itself as sound bite format for replaying each at least one prerecorded natural and/or other sound digitally stored in sound bite format.

At each of the addressable groups of memory locations "A," "B," and "C" another self-contained and complete-in-itself version of the same prerecorded natural sound is digitally stored. For example, at "A" may be digitally encoded data of a prerecorded Crack sound, at "B" a Low Rumble sound and at "C" the High Rumble sound of the same Thunder sound. To take another example, three (3) different self-contained and complete-in-themselves versions of the same Loon Call sound may be stored in sound bite format at respective ones of the groups of the addressable memory locations marked "A," "B," and "C."

Returning now briefly to FIG. 1, the device 10 of the invention is operable in one of two (2) basic modes. In one mode, any prerecorded sound stored in internal digital memory in either sound bite or loop formats is replayed by depressing the corresponding one of the sound selector switches, and in another mode, any prerecorded sound stored in external digital memory in either sound bite or loop formats of a collectable sound card inserted therewithin is replayed by depressing the sound card selector switch and by depressing the corresponding one of the sound selector switches. Any digital processor programmed to provide operation in these two (2) modes may be employed in accord with the present invention.

Figure 4:
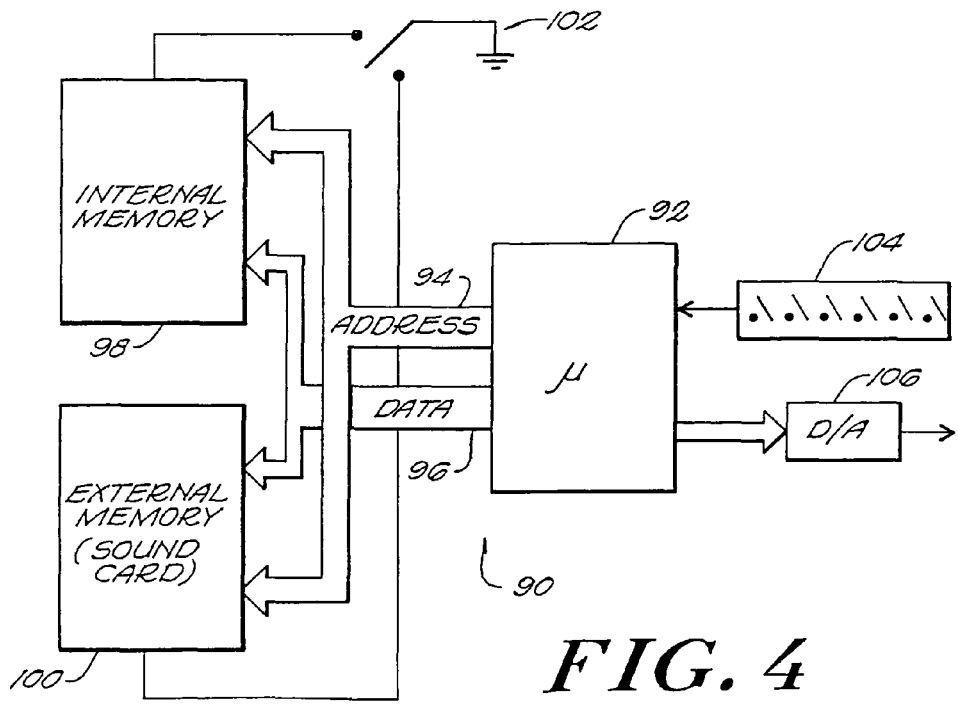
FIG. 4 is a circuit block diagram of an exemplary embodiment of the improved sound relaxation system of the FIG. 1 in accord with the present invention.

Referring now to FIG. 4, generally designated at 90 is a circuit block diagram of an exemplary embodiment of the improved digital sound relaxation system of FIGS. 1 and 2 in accord with the present invention. Processor 92 is connected via address and data lines 94, 96 to internal digital memory (RAM) 98 and to external digital memory (RAM) 100. Sound card selector switch generally designated 102 is electrically connected between ground and the chip enable terminals of the internal and external digital memories 98, 100, and a plurality of sound selector switches 104 are connected to the input port of the microcontroller 92. Program read only memory (ROM), not shown, having a main routine and loop format and sound bite format play subroutines to be described is connected in well-known manner to the address and data lines 94, 96.

A digital to analog converter 106 is coupled to the output port of the microcontroller 92. An analog amplifier and an output transducer, both not shown, are connected downstream of the digital to analog converter 106 to amplify and condition the prerecorded natural sounds selected for audible replay in well-known manner.

Figures 5, 6:
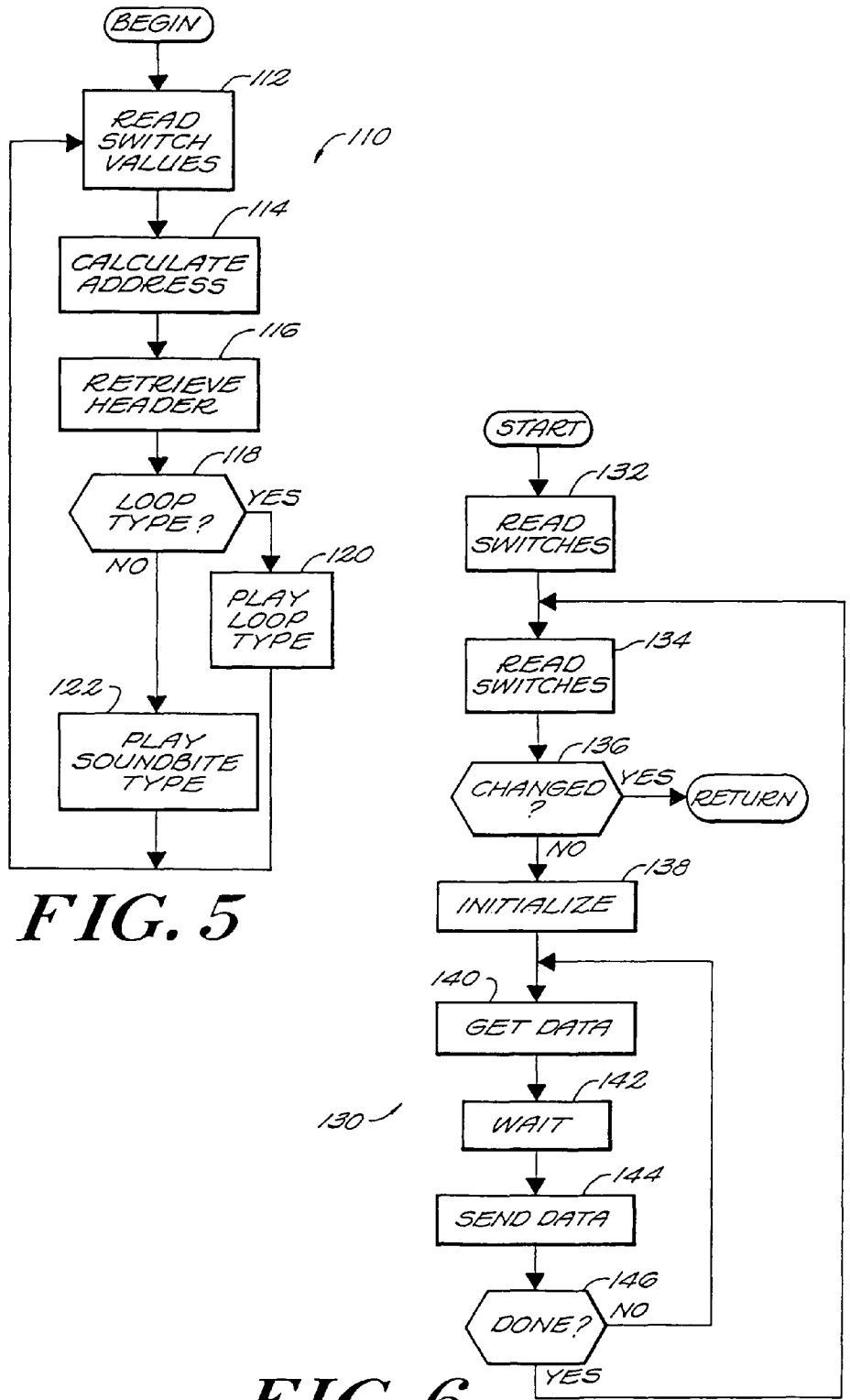
FIG. 5 is a flow chart illustrating an exemplary processor-implemented main routine of the exemplary FIG. 4 embodiment in accord with the present invention.
FIG. 6 is a flow chart illustrating an exemplary processor-implemented loop format play subroutine in accord with the present invention.

Referring now to FIG. 5, generally designated at 110 is a flowchart of the main routine implemented on the processor 92 of the FIG. 4 for playing prerecorded natural and/or other sounds digitally stored in either loop format or sound bite type format in accord with the present invention.

As shown by a block 112, the processor is operative to read the values of the depressed switches to determine which prerecorded sound digitally stored on either the external digital memory of the collectable sound card or on the internal digital memory has been selected for replay.

As shown by a block 114, the processor is then operative to calculate the address in memory of the data structure of the selected sound, and to retrieve the corresponding header portion thereof as shown by a block 116.

As shown by a block 118, the processor is then operative to determine whether the header portion of the data structure of the selected sound identifies itself as loop format, and if it does, a loop format play subroutine is called as shown by a block 120, but if it does not so identify itself, a sound bite format play subroutine is called as shown by a block 122. Processing then returns to the block 112.

Referring now to FIG. 6, generally designated at 130 is a flow chart illustrating the loop format play subroutine in accord with the present invention. As shown by blocks 132, 134, the processor is operative to read the switch values, and, as shown by a block 136, to determine whether they have changed. If the switch values read have changed, processing returns to the main routine 110 of FIG. 5.

As shown by a block 138, if the read switch values have not changed, the processor is operative to calculate the initial memory address where the data record of the selected sound is stored in loop format, and to get the data stored there as shown by a block 140.

As shown by a block 142, the processor is then operative to wait a time selected to synchronize the play-back rate to the sampling rate at which the prerecorded sound was digitally stored, and thereafter to send the data to the digital to analog converter as shown by a block 144. Although a software loop is employed in the exemplary embodiment for synchronization, it will be appreciated that hardware synchronization may be employed in accord with the present invention.

As shown by a block 146, the processor is then operative to calculate the next memory location and to determine if all of the data stored at the different data locations of the particular natural or other sound stored in loop format has been sent to the digital to analog converter, and if not, processing loops through the blocks 140, 142, 144 until that has been accomplished; otherwise, processing returns to the block 134.

Figure 7:
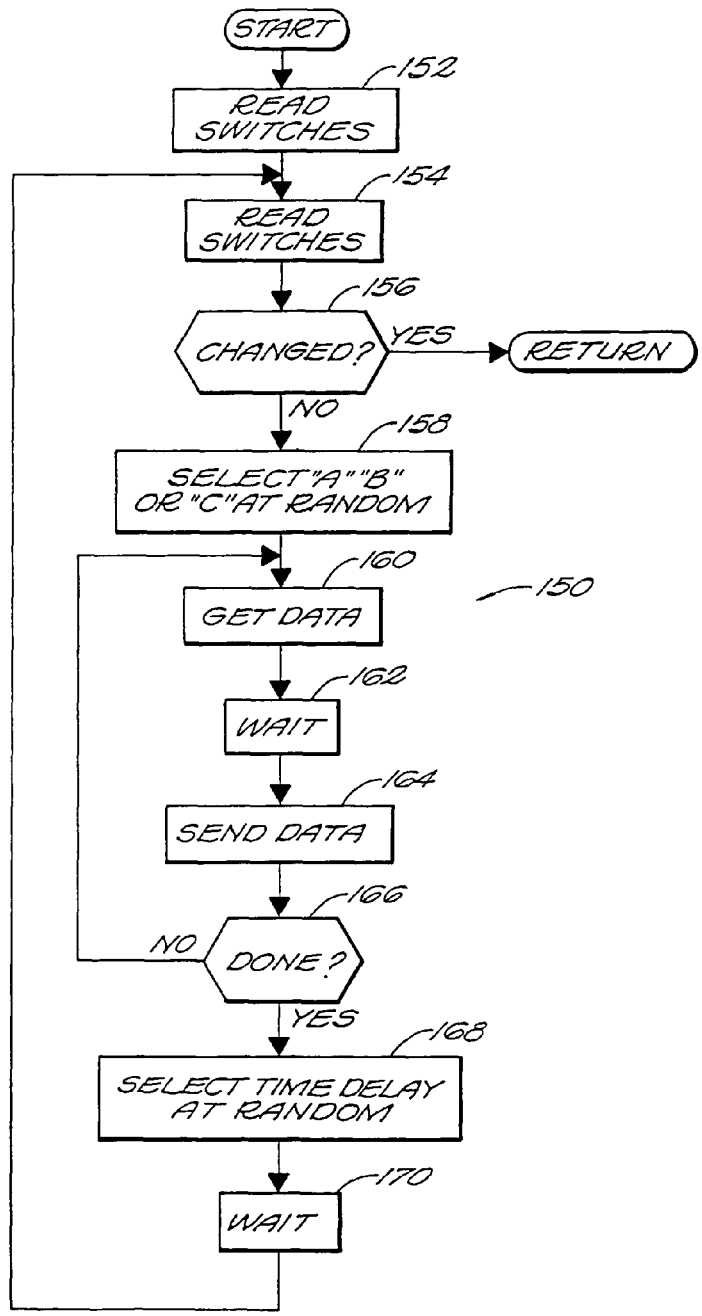
FIG. 7 is a flow chart illustrating an exemplary processor-implemented sound bite format play subroutine in accord with the present invention.

Returning now to FIG. 7, generally designated at 150 is a flow chart illustrating the sound bite play subroutine in accord with the present invention. As shown by blocks 152,154, the processor is operative to read the switch values, and, as shown by a block 156, to determine whether they have changed. If the switch values read have changed, processing returns to the main routine 110 of FIG. 5.

As shown by a block 158, if the read switch values have not changed, the processor is operative to randomly select one of the three (3) different versions of the sound selected in sound bite format for replay and to get the data stored at the first address location of the selected plurality of the three (3) pluralities of address locations as shown by a block 160.

As shown by a block 162, the processor is then operative to wait a time selected to synchronize the play-back rate to the sampling rate at which the prerecorded sound was digitally stored and thereafter to send the data to the digital to analog converter as shown by a block 164. Although a software loop is employed in the exemplary embodiment for synchronization, it will be appreciated that hardware synchronization may be employed in accord with the present invention.

As shown by a block 166, the processor is then operative to calculate the next memory location and to determine if all of the data stored at the different data locations of that particular complete-in-itself and self-contained version of the same natural (or other) sound stored in sound bite format have been sent to the digital to analog converter, and if not, processing loops through the blocks 160, 162, 164 until that has been accomplished; otherwise, the processor calculates a random time as shown by a block 168. In the presently preferred embodiments, the time delay is selected at random between four (4) and twenty (20) seconds, although another range of values and other delays could be selected in accord in accord with the present invention.

Figure 8:
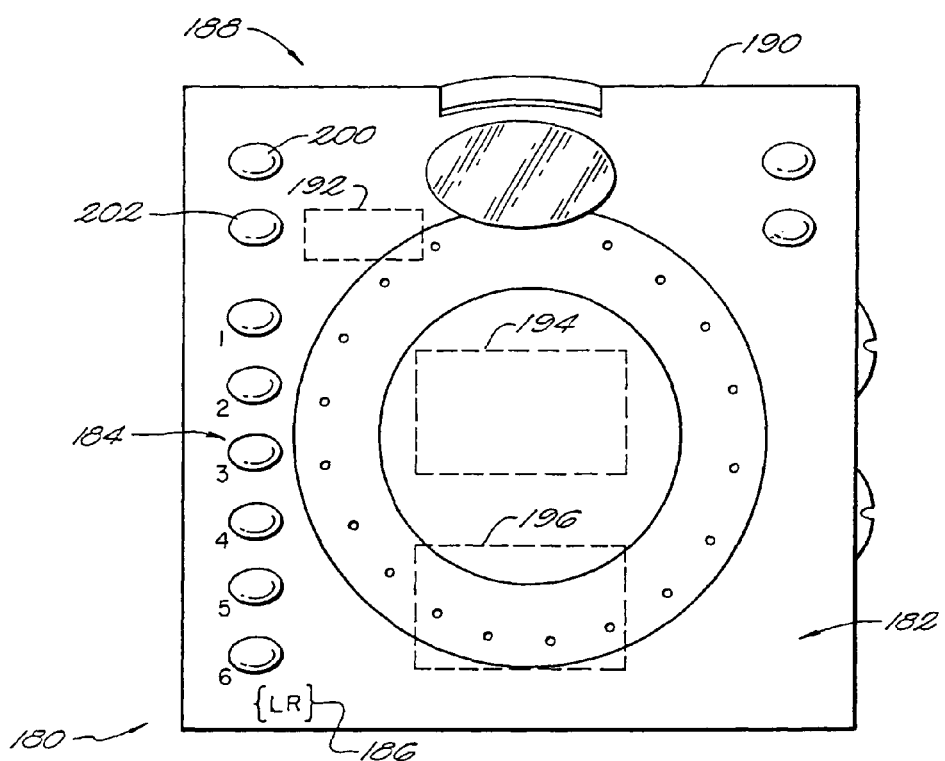
FIG. 8 is a front elevational view of another embodiment of an improved sound relaxation system in accord with the present invention that not only provides individuals the capability to customize their library of natural sounds, as in the embodiment of the FIG. 1, but also provides individuals the capability to select at least two (2) natural sounds of their library of natural sounds for concurrent replay in accord with the present invention.

Referring now to FIG. 8, generally designated at 180 is a front elevational view of another embodiment of an improved digital sound relaxation system in accord with the present invention. The device 180 not only provides individuals the capability to customize their library of natural sounds, by inserting any one of one or more collectable sound cards thereinto as in the device 10 of the FIGS. 1 and 2, but also provides individuals the capability to select two (2) (or more) natural or other sounds of their library (whether provided in internal, or internal and external memory) of natural and/or other sounds for concurrent replay.

The improved system 180 includes a housing generally designated 182 and a plurality of single-pole double-throw sound selector switches generally designated 184 arranged in laterally spaced apart relation proximate the left edge of the housing 182. Each of the switches 184 provides selection of one sound, when toggled to the left, and selection of another sound, when toggled to the right, as schematically illustrated by bracket 186. Although six (6) individual dual-position sound selector switches 184 providing selection of twelve (12) natural and/or other sounds are presently preferred, any number or kind of input device or devices may be employed in accord with the present invention.

A collectable sound card receiving port generally designated 188 is provided through the top wall 190 of the housing 182. Although it is preferred to locate the port 188 through the top wall 190 of the housing 182, any other collectable sound card receiving interface that is user-friendly, and easy-to-access, may be employed in accord with the present invention.

An electrical connector schematically illustrated in dashed outline 192 is provided in the port 188 of the housing 182. The electrical connector 192 is adapted to mate with the electrical connector 32 (FIG. 2) of the collectable sound card 30 (FIG. 2), which is not described again for the sake of brevity of disclosure.

The device 180 includes two (2) internal digital memories schematically illustrated in dashed lines 194, 196. In the exemplary embodiment described hereinbelow, a plurality of prerecorded natural or other sounds are digitally stored in loop format in one of the internal digital memories 194, 196 and a plurality of prerecorded natural or other sounds are digitally stored in sound bite format in the other one of the internal digital memories 194, 196. Although two (2) internal digital memories are disclosed in the exemplary embodiment, a different number of internal digital memory devices could be employed in accord with the present invention. The loop format and sound bite format are described above in connection with the description of the FIG. 3 and are not again described for the sake of brevity of disclosure.

A sound card selector switch 200 is mounted to the top wall 190 of the housing 182. In the "off" condition of the sound card selector switch 200, toggling any one of the switches 184 to the left selects another one of the prerecorded natural sounds stored in the memory 194 for replay, and toggling any one of the switches 184 to the right selects another one of the prerecorded natural sounds stored in the memory 196 for replay. In the "on" condition of the sound card selector switch 200, which reassigns the switches 184 from the internal memory 194 to the external memory of a collectable sound card inserted in the port 188, toggling any one of the switches 184 to the left selects another one of the prerecorded natural sounds stored in the external memory 34 (FIG. 2) of the collectable sound card for replay. In this manner, the same sound selector switches 184 are enabled to select among the plurality of prerecorded natural sounds contained either in the internal memory of the device 180 or in the external memory 34 (FIG. 2) of each collectable sound card that may be inserted therewithin. The left positions of the six (6) switches 184 in the presently preferred embodiment, as reassignable by the selector switch 200, are able to select among twelve (12) prerecorded sounds, and the right positions of the six (6) switches 184 are able to select among another six (6) prerecorded sounds, thereby making available a total of eighteen (18) prerecorded sounds for selectable replay.

A combine switch 202 is mounted to the front of the housing 182 of the device 180. The combine switch enables individuals to select for concurrent replay one of the sounds selected by toggling one of the switches of the plurality of switches 184 to the left, with one of the sounds selected by toggling one of the switches of the plurality of switches 184 to the right, thereby making available a total of thirty-six (36) composite sounds for selectable replay.

The sound card selector switch 200 and the combine switch 202 enable individuals to select for concurrent replay any one of the sounds prerecorded in either the internal or external memories 194, 34 (FIG. 3), as determined by the left toggle positions of the plurality of switches 184 that may be reassigned, as described above, from internal to external memory by the sound card selector switch 200, with any one of the sounds prerecorded in the internal memory 196, as determined by the right toggle positions of the plurality of switches 18, and by the combine switch 202. The left toggle positions of the six (6) switches 184 in the presently preferred embodiment, as reassignable by the sound card selector switch 200, are able to select among twelve (12) prerecorded sounds, which twelve (12) sounds are each combinable, by depressing the combine switch 202, with another one of the six (6) sounds selected by toggling the six (6) sound selector switches 184 to the right, thereby making available a total of seventy-two (72) composite sounds for selectable replay.

Taking the eighteen (18) sounds available by toggling any one of the six (6) switches 184 to the left, as reassignable by the selector switch 200, and by toggling any one of the six (6) switches 184 to the right, together with the seventy-two (72) composite sounds available by toggling any one the six (6) switches 184 to the left, as reassignable by the selector switch 200, and combining the same, by depressing the combine switch 202, with another one of the six (6) sounds selected by toggling another one of the six (6) sound selector switches 184 to the right, makes for a grand total of ninety (90) different sounds in the presently preferred embodiment.

The device 180 of the invention is operable in one of four (4) basic modes. In one mode, any prerecorded sound stored in the first internal digital memory is replayed by toggling the corresponding one of the sound selector switches assigned thereto to the left, in another mode, any prerecorded sound stored in external digital memory of a collectable sound card inserted therewithin is replayed by depressing the sound card selector switch and by toggling the corresponding one of the sound selector switches to the left, in a third mode, any prerecorded sound stored in the second internal digital memory is replayed by toggling the corresponding one of the sound selector switches assigned thereto to the right, and in a fourth mode, two (2) or more sounds stored in either internal or external memory may be combined for concurrent replay by toggling the sound selector switches to the left, by depressing the combine switch, and by toggling the sound selector switches to the right; and by depressing the sound card selector switch, by toggling the sound selector switches to the left, by depressing the combine switch, and by toggling the sound selector switches to the right. Any processor programmed to provide operation in these four (4) modes may be employed in accord with the present invention.

In any of the foregoing modes of operation, the sound selected for replay is reproduced through dual, phase-shifted stereo speakers, not shown, to provide realistic playback. In the presently preferred embodiment, the sounds stored in the memory 194 are Ocean Surf, Steam, Rain on Water, Waterfall, Summer Night and Wind sounds, the sounds stored in the memory 196 are Sea Gulls, Song Birds, Thunder, Fog Horn, Loons and Rain on Forest Floor sounds, and the sounds stored on the collectable sound card are grouped themewise, such as the Thunderstorm in the Wilderness, Forest Rain, Waterfall, Loons on Wilderness Lake, Mountain Valley Windstorm, and Roaring Bonfire sounds of the so-called Wilderness Retreat collectable sound card. In the illustrated embodiment, the device 180 includes a lighted clock, a dual alarm/snooze button, an AM/FM radio, headphone jacks, an off/resume button, a four position timer, and bass/treble controls, all not further described as forming no part of the present invention.

Figure 9:
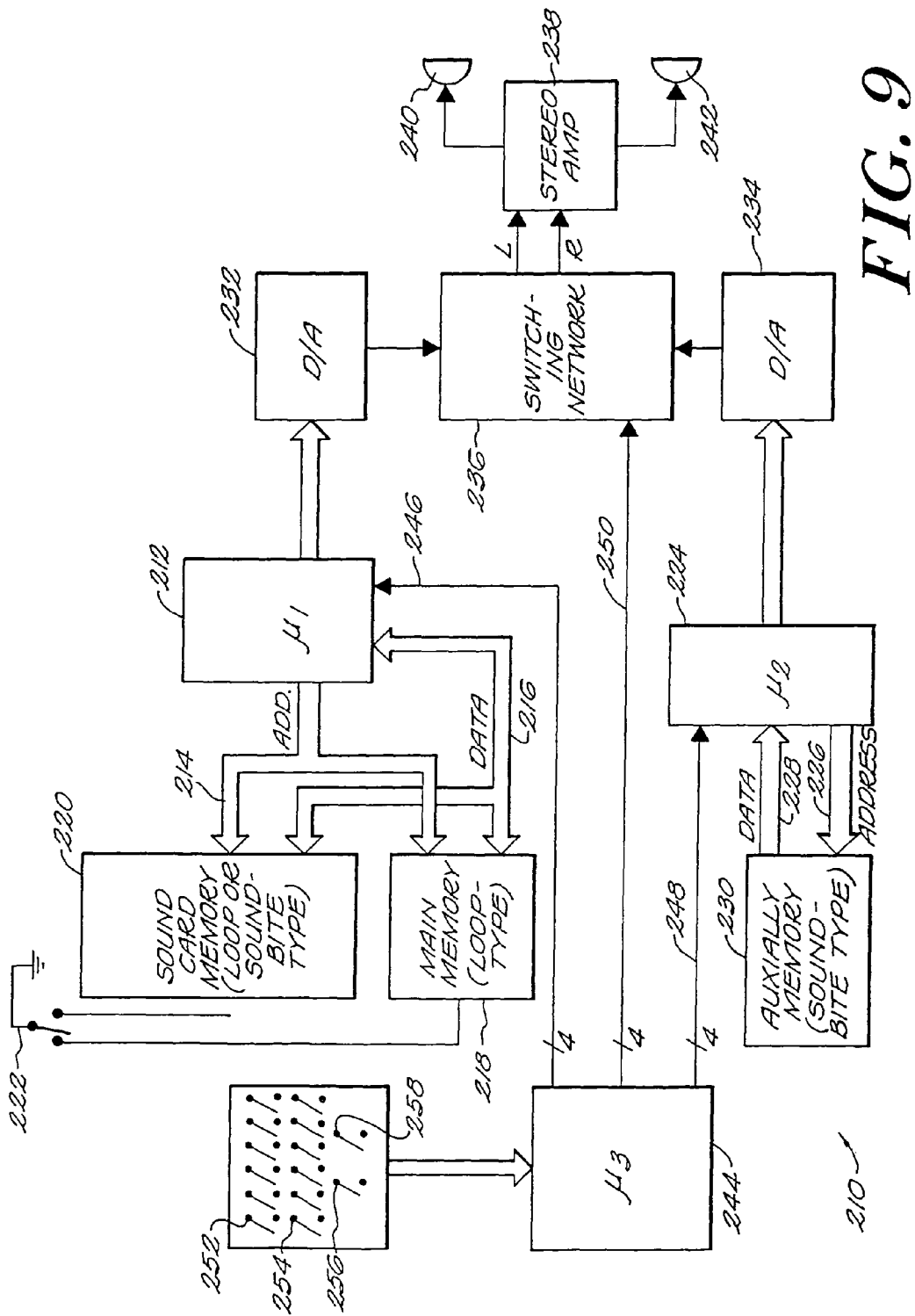
FIG. 9 is a circuit block diagram of an exemplary embodiment of the improved digital sound relaxation system of the FIG. 8 in accord with the present invention.

Referring now to FIG. 9, generally designated at 210 is a circuit block diagram of an exemplary embodiment of the improved-flexibility digital sound relaxation system of the FIG. 8 in accord with the present invention. A first processor 212 is connected via address and data lines 214, 216 to internal digital memory (RAM) 218 and to external digital memory (RAM) 220. Sound card selector switch 222 is electrically connected between ground and the chip enable terminals of the internal and external digital memories 218, 220. Program read only memory (ROM), not shown, is connected in well-known manner to the address and data lines 214, 216. As appears more fully below, the first processor 212 is dedicated to replay the sounds stored in either the memory 218 or the external memory 220 of a collectable sound card, in either or both of the loop and sound bite formats.

A second processor 224 is connected via address and data lines 226, 228 to internal digital memory (RAM) 230. Program read only memory (ROM), not shown, is connected to the address and data lines 226, 228 in well-known manner. As appears more fully below, the second processor 224 is dedicated to replay the sounds stored in the memory 230.

A digital to analog converter 232 is coupled to an output port of the processor 212, and a digital to analog converter 234 is coupled to an output port of the processor 224.

A switching network 236 is coupled to each of the digital to analog converters 232, 234, and a stereo amplifier 238, to which dual speakers 240, 242 are connected, is connected to the switching network 236. In the exemplary embodiment, the switching network 236 is preferably implemented by IC 4066 Quad switches and the stereo amplifier by the Sony CXA167M/P IC. The switching network 236 enables sound playback through both channels of the stereo amplifier if either processor 212, processor 224 or both processors 212 and 224 are enabled in a manner to be described.

A master control processor 244 is coupled to the first dedicated processor 212 via control lines 246, to the second dedicated processor 224 via control lines 248 and to the switching network via control lines 250. A first plurality of sound selector switches 252 preassigned to another one of the natural or other sounds stored in the memory 218 of the processor 212, a second plurality of sound selector switches 254 preassigned to another one of the natural or other sounds stored in the memory 230 of the processor 224, a sound card selector switch 256 and a combine switch 258 are connected to an input port of the processor 244.

The master control processor 244 decodes the switch values selected, latches the same and provides control input, via the control lines 246, 250, to the first and second dedicated processors 212, 224, that instructs the dedicated processors 212, 224 to play or to not play the particular sounds selected either in stand-alone mode, when sounds of either dedicated processor 212, 224 have been selected, or in combined playback mode, when sounds of both dedicated processors 212, 224 have been selected, and provides control input, via the control lines 248, to the switching network 236 that configures the same to provide dual-channel playback for either the stand-alone playback modes of each of the dedicated processors 212, 224 or the combined playback mode of both of the dedicated processors 212, 224.

Figure 10:
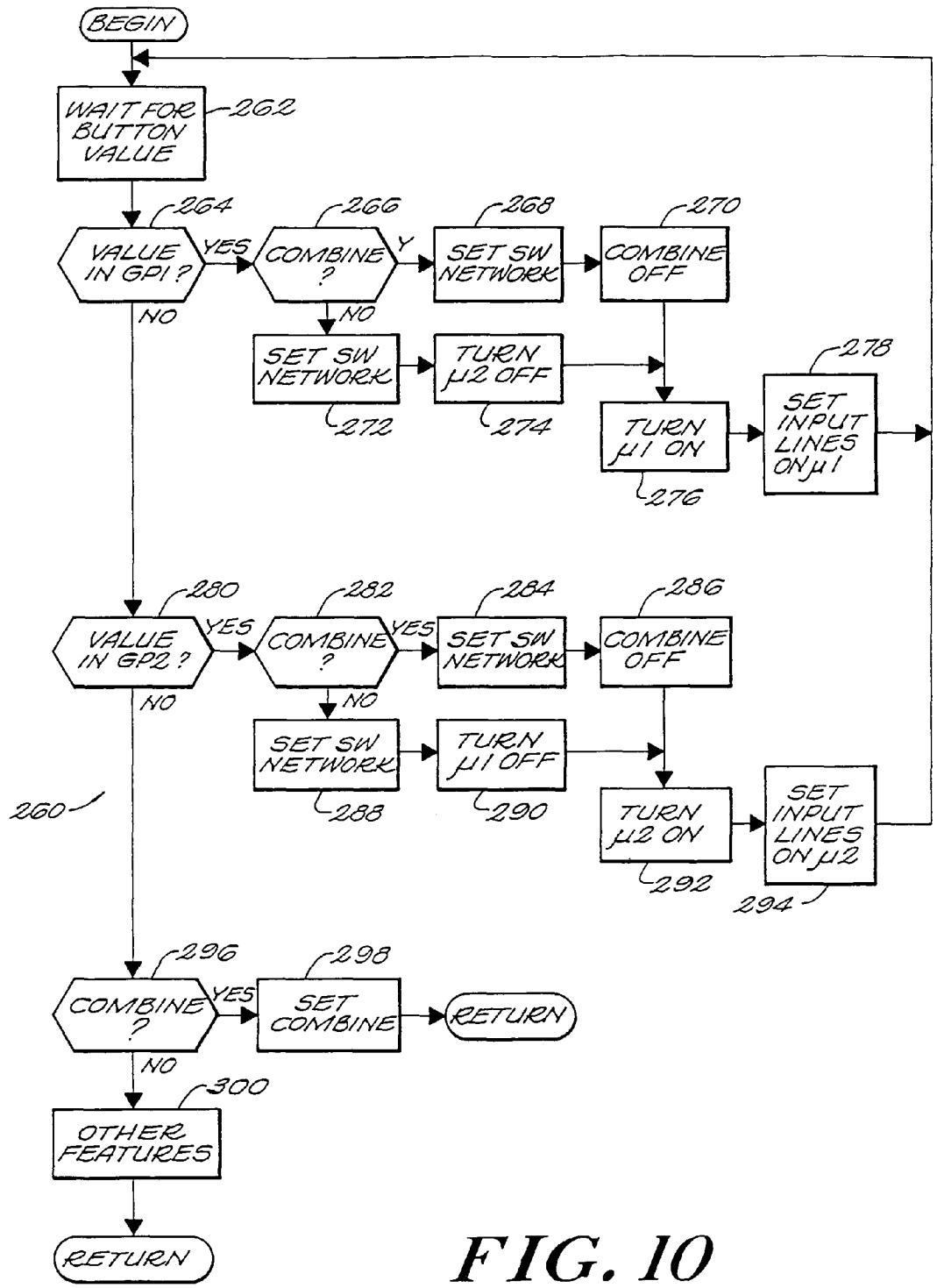
FIG. 10 is a flow chart illustrating an exemplary processor-implemented main routine of the exemplary FIG. 8 embodiment in accord with the present invention.

Referring now to FIG. 10, generally designated at 260 is a flowchart of the main routine of the master control processor in accord with the exemplary embodiment of the present invention. As shown by a block 262, the master control processor is operative to wait for a button to be activated.

As shown by a block 264, the processor is operative to determine if the activated button corresponds to the group of sounds preassigned to the first dedicated sound playback processor and if it is, determines whether the combine switch has been previously depressed as shown by a block 266.

As shown by a block 268, if the combine switch has been previously depressed, the master control processor sets the switching network to switch the sound played by one of the dedicated processors to one channel and the sound played by the other of the dedicated processors to the other channel of the stereo amplifier and turns the combine mode "off" as shown by a block 270.

As shown by a block 272, if the combine switch has not been depressed, the master control processor is operative to set the switching network to switch the selected sound played by the first dedicated processor to both the channels of the stereo amplifier, and to turn the second dedicated processor "off" as shown by the block 274.

As shown by the block 276, the master control processor is then operative to turn the first dedicated sound playback processor "on" and to set the input control lines thereto to identify the sound selected as shown by the block 278.

As shown by a block 280, if the activated button does not correspond to the group of sounds preassigned to the first dedicated sound playback processor, the master control processor is operative to determine if it corresponds to the group of sounds preassigned to the second dedicated sound playback processor.

If it does, the master control processor is operative to determine whether the combine switch has been previously depressed as shown by a block 282.

As shown by a block 284, if the combine switch has been previously depressed, the master control processor sets the switching network to switch the sound played by one of the dedicated processors to one channel and the sound played by the other of the dedicated processors to the other channel of the stereo amplifier, and turns the combine mode "off" as shown by a block 286.

As shown by a block 288, if the combine switch has not been depressed, the master control processor is operative to set the switching network to switch the selected sound played by the second dedicated processor to both of the channels of the stereo amplifier, and to turn the first dedicated processor "off" as shown by the block 290.

As shown by the block 292, the master control processor is then operative to turn the second dedicated sound playback processor "on" and to set the input control lines thereto to identify the sound selected as shown by the block 294.

As shown by a block 296, if the activated button does not correspond to the group of sounds preassigned to either the first or the second dedicated sound playback processors, the master control processor is operative to determine if the combine switch has been depressed. If it has, as shown by the block 298, the master control processor is operative to flag the combine mode, and processing returns to the block 262; otherwise, and as shown by the block 300, the master control processor is operative to determine if any of the switches that correspond to the alarm clock, radio and other features of the improved-flexibility sound relaxation have been activated, and takes the corresponding control action as shown by the block 300, which block 300, forming no part of the present invention, is not further described herein, and processing returns to the block 262.

The main routine for each of the dedicated first and sound playback processors is the same as the main routine described above in connection with the description of FIG. 5, except that instead of reading the switch values each of the dedicated sound playback processors reads its input control lines to determine whether it has been enabled and if so, to determine which of its group of sounds has been selected. The loop format and sound bite format subroutines called thereby are the same as the loop format and sound bite format subroutines described above in connection with the description of the FIGS. 6 and 7, with the exception that instead of reading the switch values each of the dedicated sound playback processors reads its input control lines. The main routine, and the loop format and sound bite format subroutines, are not again described herein for the sake of brevity of explication.

Figure 11B:
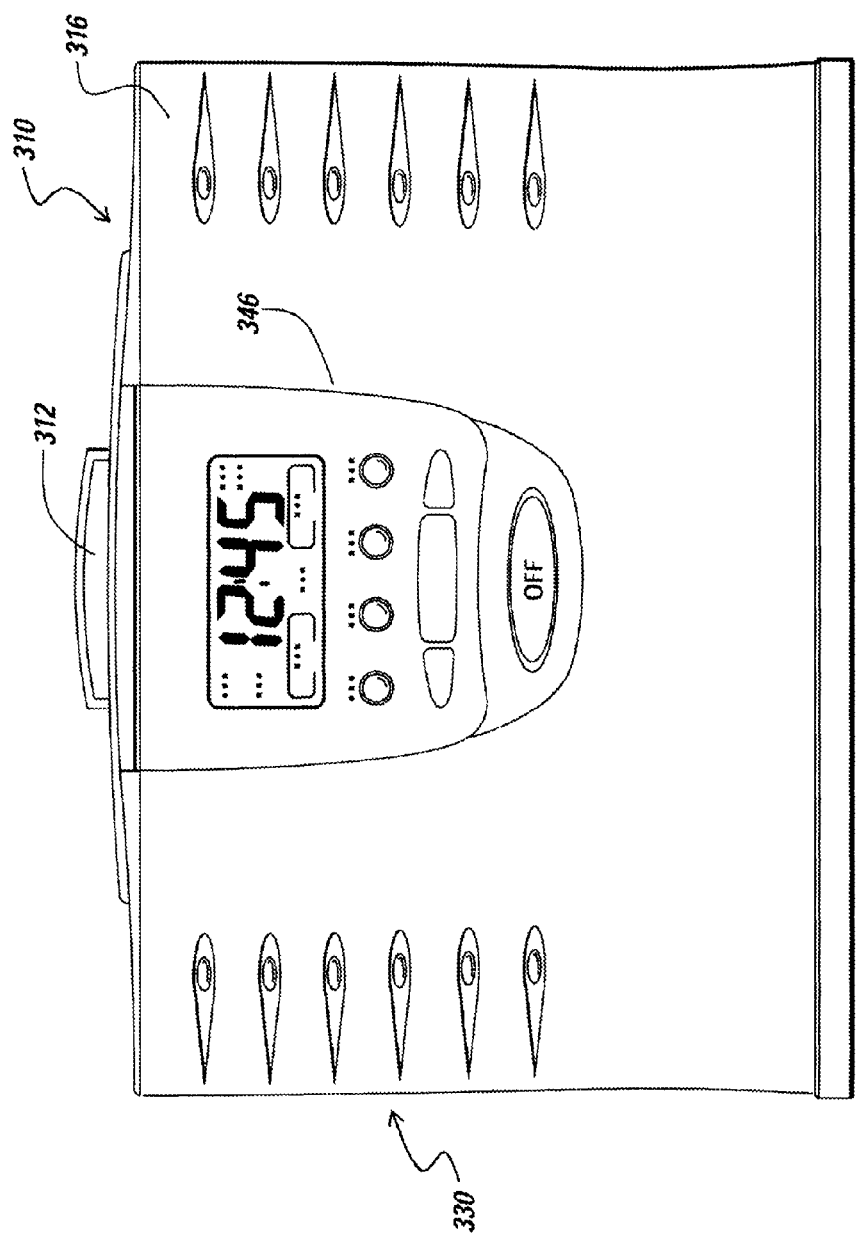
FIG. 11 illustrates in the FIGS. 11A and 11B thereof top plan and front elevational views of one exemplary embodiment of a digital sound relaxation and sleep-inducing system in accord with the present invention.

Referring now to FIGS. 11A and 11B, generally designated at 310 are top plan and front elevational views of an exemplary embodiment of a digital sound relaxation and sleep-inducing system in accord with the present invention. The embodiment 310 shares the same hardware architecture as the embodiment 180 described above in connection with the description of FIG. 9, not separately described again for the sake of brevity of explication, and is operable in each of the four modes described above in connection with the description of FIG. 8, which modes, briefly stated, are to replay sound card sounds, to replay main sounds stored in main memory, to replay auxiliary sounds stored in auxiliary memory, and to replay any combination of main and auxiliary sounds and any combination of sound card and auxiliary sounds. As in the embodiment 180, the sounds may be continuous or intermittent sounds respectively stored in the loop and sound bite formats described above in connection with the description of FIG. 3, which loop and sound bite formats are not described again for the sake of brevity of explication.

The embodiment 310 differs from the embodiment 180 in three principal respects. First, it includes a user interface having combination mode setting and sequential sound selector switches to be described instead of separately provided mode selector and sound selector switches as in the embodiment 180. Second, the embodiment 310 is operable to generate a sleep-induce sound pattern to be described, in addition to a noise-masking and sound-soothing sound pattern as in the embodiment 180, which sleep-induce sound pattern in a manner to be described synergistically co-acts with the listener's biorhythms to induce a state of deep relaxation that helps the listener to fall asleep. And third, the embodiment 310 is operable in alarm-set and alarm-check modes to be described respectively to replay any previously selected prerecorded sound of its library of sounds as the alarm wake-up sound and to provide one-touch visual and/or audible display of alarm wake-up parameters.

The embodiment 310 includes a sound card 312 and a sound card receiving port generally designated 314 preferably mounted to the top face of the housing 316 that enables listeners to customize the library of available prerecorded sounds to individual taste. As in the embodiments described above, the sound card 312 includes a digital memory, not shown, in which a plurality of samples of prerecorded sounds are digitally stored in loop-format and/or sound bite format, and, in which, in a sleep-induce sound card embodiment, a data table to be described that is used to implement the presently preferred embodiment of the sleep-induce sound pattern is stored. Other digital information to provide sleep-induce sounds may be stored therein without departing from the inventive concepts.

The user interface for both sound relaxation mode operation and sleep-induce mode operation will now be described. A combination sound card sound mode select and sequential sound card sound selector switch 318 is mounted to the top face of the housing 316. A combination main sound mode select and sequential main sound selector switch 320 is mounted to the top face of the housing 316. A combination auxiliary sound mode select and sequential auxiliary sound selector switch 322 is mounted to the top face of the housing 316. A combine mode selector switch 324 is mounted to the top face of the housing 316. A combination sleep-induce sound mode and sequential sleep-induce sound selector switch 326 is mounted to the top face of the housing 316. A rotary volume switch is mounted to the side of the housing 316, not shown, and a listener volume select switch 328 is mounted to the top face of the housing 316. The rotary volume switch allows the listener to control the listening and wake-up volumes, while the listener volume select switch 328 allows the listener to select a listening volume different from the listening and wake-up volume set by the rotary volume switch. In the presently preferred embodiment, the listener volume select switch 328 provides three levels of preset attenuation of the volume set by the rotary volume switch. In a typical case, the listening volume may be lowered at bedtime via the listener volume select switch 328 without affecting the wake-up volume. A bank of LED's generally designated 330 arranged as a vertical array is mounted to the left front of the housing 316, and a bank of LED's generally designated 332 arranged as a vertical array is mounted to the right front of the housing 316. Printed indicia, preferably Ocean Surf, Stream, Shower, Waterfall, Woodlands, and Wind, representative of the prerecorded sounds stored in main memory, is provided adjacent each of the LED's of the bank 330, and printed indicia, preferably Sea Gulls, Song Birds, Thunder, Fog Horn, Loon, and Rain, representative of the prerecorded sounds stored in auxiliary memory, is provided adjacent each of the LED's of the bank 332.

To enter sound card sound replay mode, the combination sound card mode select and sequential sound card selector switch 318 is depressed. The system 310 then replays at initialization a default sound card sound; if not at initialization, the previously played sound card sound is replayed. The sound card sounds are arraigned as a stack, and with every depression of the switch 318 the next sound of the sound card sound stack is replayed. If the switch 318 is depressed at a time that the sound at the bottom of the sound card sound stack is being replayed, the sound at the top of the sound card stack is replayed. With every depression of the combination sound card mode select and sequential sound card sound selector switch 318, another LED of the left bank of LED's 330 is lit and the corresponding sound is replayed.

To enter main sound replay mode, the combination main sound mode select and sequential main sound selector switch 320 is depressed. The system 310 then replays at initialization a default main sound; if not at initialization, the previously played main sound is replayed. The main sounds are arraigned as a stack, and with every depression of the switch 320 the next sound of the main sound stack is replayed. If the switch 320 is depressed at a time that the sound at the bottom of the main sound stack is being replayed, the sound at the top of the main stack is replayed. With every depression of the combination main sound mode select and sequential main sound selector switch 320, another LED of the left bank of LED's 330 is lit and the corresponding sound is replayed.

To enter auxiliary sound replay mode, the combination auxiliary sound mode select and sequential auxiliary sound selector switch 322 is depressed. The system 310 then replays at initialization a default auxiliary sound; if not at initialization, the previously played auxiliary sound is replayed. The auxiliary sounds are arraigned as a stack, and with every depression of the switch 322 the next sound of the auxiliary sound stack is replayed. If the switch 322 is depressed at a time that the sound at the bottom of the auxiliary sound stack is being replayed, the sound at the top of the auxiliary stack is replayed. With every depression of the combination auxiliary sound mode select and sequential auxiliary sound selector switch 322, another LED of the right bank of LED's 332 is lit and the corresponding sound is replayed.

For each of the single-sound replay modes (sound card, main sound and auxiliary sound modes), only one light per bank of LED's is lit indicating the sound selected. In combine mode described below, one LED of each of the left and right banks of LEDs is lit indicating the combined sound selected for replay.

To enter combine sound replay mode, the combine mode switch 324 is depressed. The system 310 then replays at initialization a default combine sound; if not at initialization, the previously played combine sound is replayed. To change the mix of sounds, if main sounds and auxiliary sounds are combined, depression of either the main sound sequential selector switch 320 or the auxiliary sound sequential selector switch 322 replaces the next sound in the stack with the one currently being replayed, and changes the associated LED's, and if sound card sounds and auxiliary sounds are combined, depression of either the sound card sequential sound selector switch 318 or the auxiliary sound sequential sound selector switch 322 replaces the next sound in the stack with the one currently being replayed, and changes the associated LED's. In combine mode, as will be appreciated, one LED of each of the banks of LED's 330,332 is lit corresponding to the mix of sounds being replayed in combine mode, whether main/auxiliary or sound card/auxiliary, and the corresponding combine sound is replayed.

To enter sleep-induce mode, the combination sleep-induce mode select and sequential sleep-induce sound selector switch 326 is depressed. In the presently preferred embodiment, although other sleep-induce techniques may be employed without departing from the inventive concepts, the sleep-induce sounds are the same sounds as the sounds in the main sound stack and the system 310 imparts a sleep-induce pattern to any main sound selected via depression of the sequential sleep-induce sound selector switch 326. In sleep-induce mode as appears more fully below, the system 310 replays the selected main sound for a predetermined first time interval at record rate and lights the corresponding LED of the bank 330 of LED's. Thereafter, the system 310 imparts a sleep-induce pattern to the main sound selected, replaying it for a second time interval at progressively slower replay rates in successive third time intervals. The sleep-induce pattern imparted to the selected sound synergistically co-acts with the listener's biorhythms to induce a state of deep relaxation which helps the listener to fall asleep. The replay of the selected sound at progressively slower replay rates in successive time intervals brings the brainwaves of the listener to the same place that the brain usually goes when it is in a sleep state. Reference in this connection may be had to an article entitled "A Pilot Study Of EEG Entrainment As a Sleep Aid," by Clinton et al., appearing at Abstracts, Associated Professional Sleep Societies, 11$^{th}$ Annual Meeting (San Francisco: Jun. 10-15, 1997), to product advertisements for stress relief CD's entitled "Natural Stress Relief," and "Delta Sync Sleep System," and to U.S. Pat. Nos. 5,036,858, 5,163,426, 5,167,228, 5,176,133, 5,213,562, and 5,356,368, each incorporated herein by reference, for a description of the phenomenon of brainwave entrainment that is believed to be responsible for inducing sleep in the present invention.

The user interface for alarm mode operation will now be described. The system 310 includes two separate alarms, alarm "one" and alarm "two." For each, the alarm wake-up sound may be a buzzer sound, selected by depression of a respective buzzer select button 331,333; a radio wake-up sound, selected by depression of a respective radio select button 334,336; and any sound of the library of prerecorded sounds (main, auxiliary, sound card, or combination of main and auxiliary or sound card and auxiliary sounds) available for replay by depression of alarm sound select buttons 338, 340, each of which is provided in the top of the housing 316. As will be appreciated, the listener operates the mode select and sound selector buttons 318 through 324 in the manner described above to replay any selectable sound of the library of prerecorded sounds, and then, by depression of the alarm sound select buttons 338, 340, saves that sound as the wake-up-sound for respective ones of the alarms. An alarm-check button 342,344 is provided in the top face of the housing 316 for each alarm. As appears more fully below, the system 310 is operative in response to depression of the alarm-check buttons 342,344 to provide a visual indication of alarm "one" or "two" status parameters on display generally designated 346 mounted to the front face of the housing 316 that includes whether the alarm is active or inactive, the wake-up time, and mode selected, whether buzzer, radio or sound wake-up, as well as to provide audible playback of the sound selected (buzzer, radio or sound wake-up) at wake-up volume level.

Other features of the user-interface, including radio presets and tuning, a 30-60-90-continuous interval timer, 12/24 time display, time and alarm sets, snooze/resume, auxiliary volume control, and input/output ports, are not further described herein as forming no part of the present invention.

Figure 12:
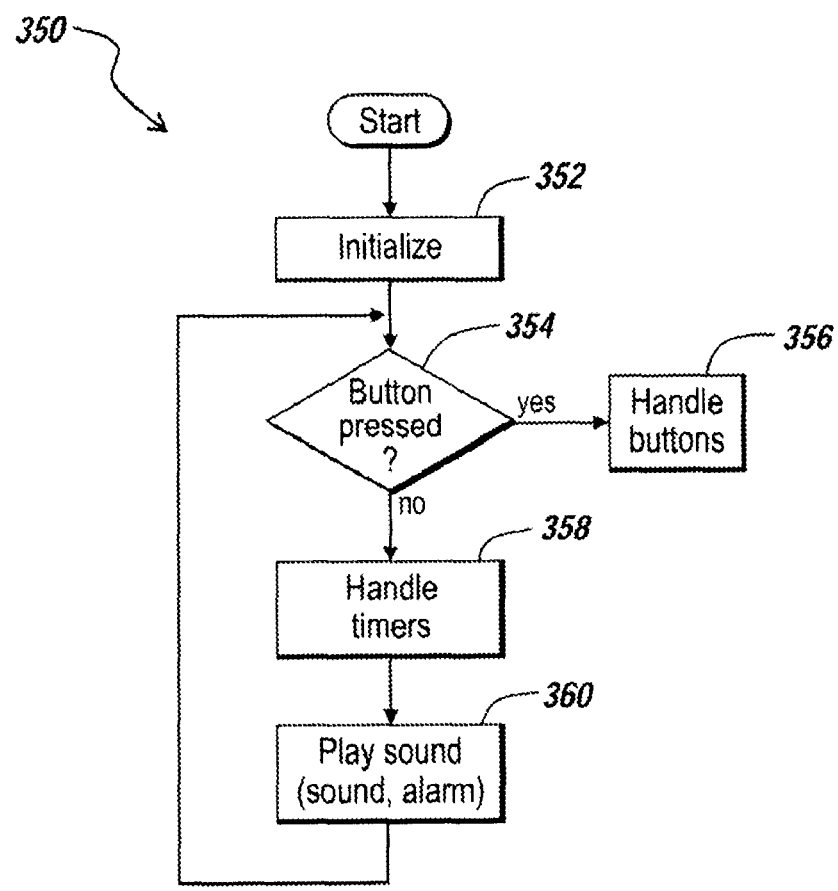
FIG. 12 is a flow chart illustrating an exemplary processor-implemented main routine of the exemplary FIG. 11 embodiment in accord with the present invention.

Referring now to FIG. 12, generally designated at 350 is a flow chart of an exemplary main routine of the digital sound relaxation and sleep-inducing system in accord with the present invention.

As shown by block 352, the processor is operative to initialize its registers and to display time and alarm status information in idle mode. The registers include registers that represent mode, whether main; sound card; auxiliary; idle; combine, main or sound card and auxiliary; or sleep-induce modes; and registers that include indices that represent which one or more sound of the library of prerecorded sounds in which mode is to be replayed, including a main index; a sound card index; an auxiliary index; a sleep-induce index; and a combine main/auxiliary and a combine sound card/auxiliary index. The indices are set to default sounds upon initial start-up.

As shown by block 354, the processor is then operative to determine whether a button has been depressed. If so, the processor is operative to execute a handle buttons subroutine to be described as shown by a block 356.

As shown by block 358, the processor otherwise is operative to handle timers. The timers include snooze, 30/60/90 interval, and alarm wake-up timers. Preferably, the timers are implemented as interrupts that interrupt processing to handle the interrupts as they arise.

As shown by block 360, the processor otherwise is operative to play sounds. For alarm wake-up sounds and for sounds other than sleep-induce sounds, the processor-implemented loop and sound bite format play subroutines described above in connection with the description of FIGS. 1-7, not separately described again for the sake of brevity of explication, are employed. For sleep-induce sound replay, the processor implements a sleep-induce sound replay subroutine to be described. Processing then returns to block 354.

Figure 13:
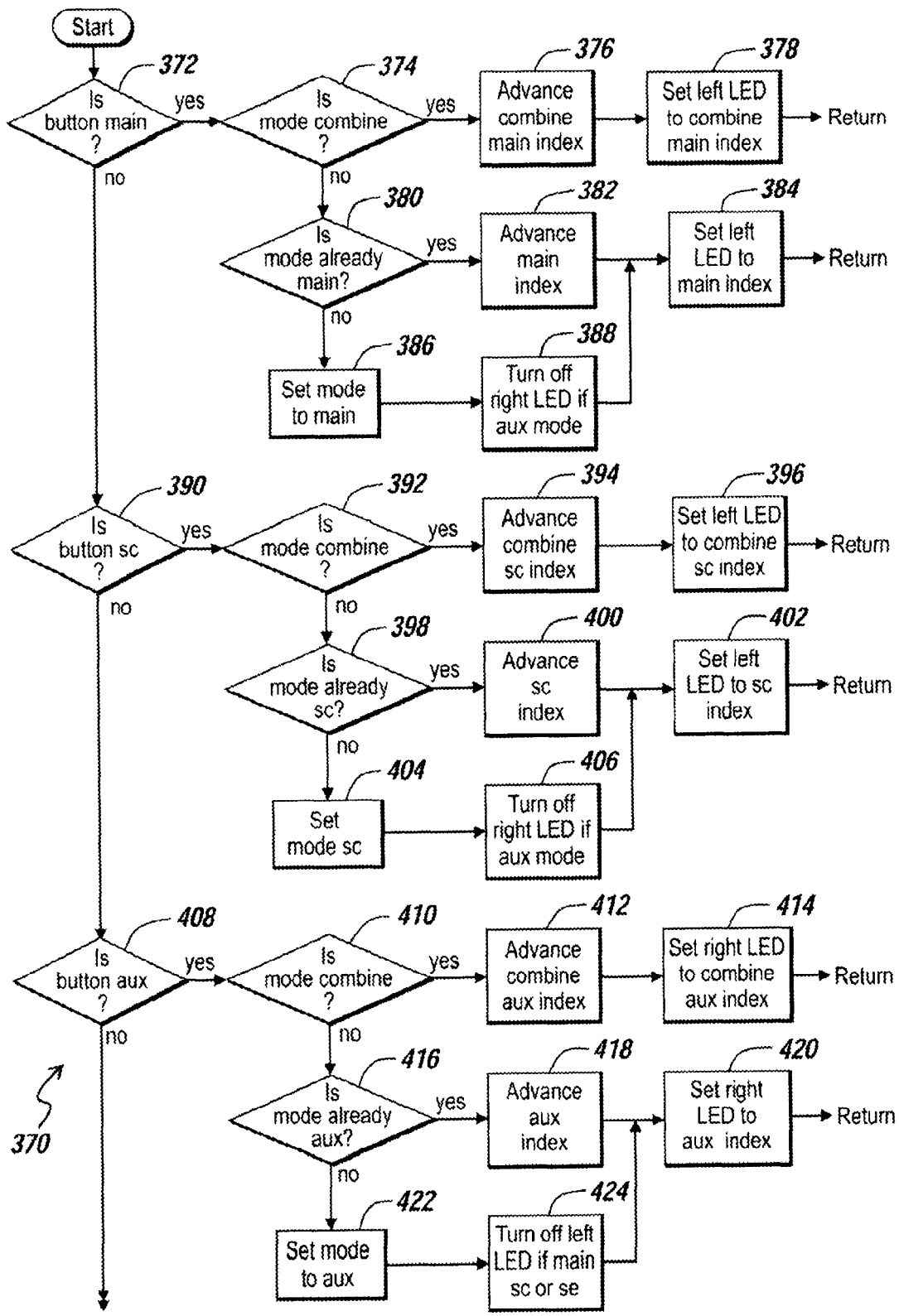
FIG. 13 is a flow chart illustrating an exemplary processor-implemented handle buttons subroutine in accord with the present invention.
Figure 13:
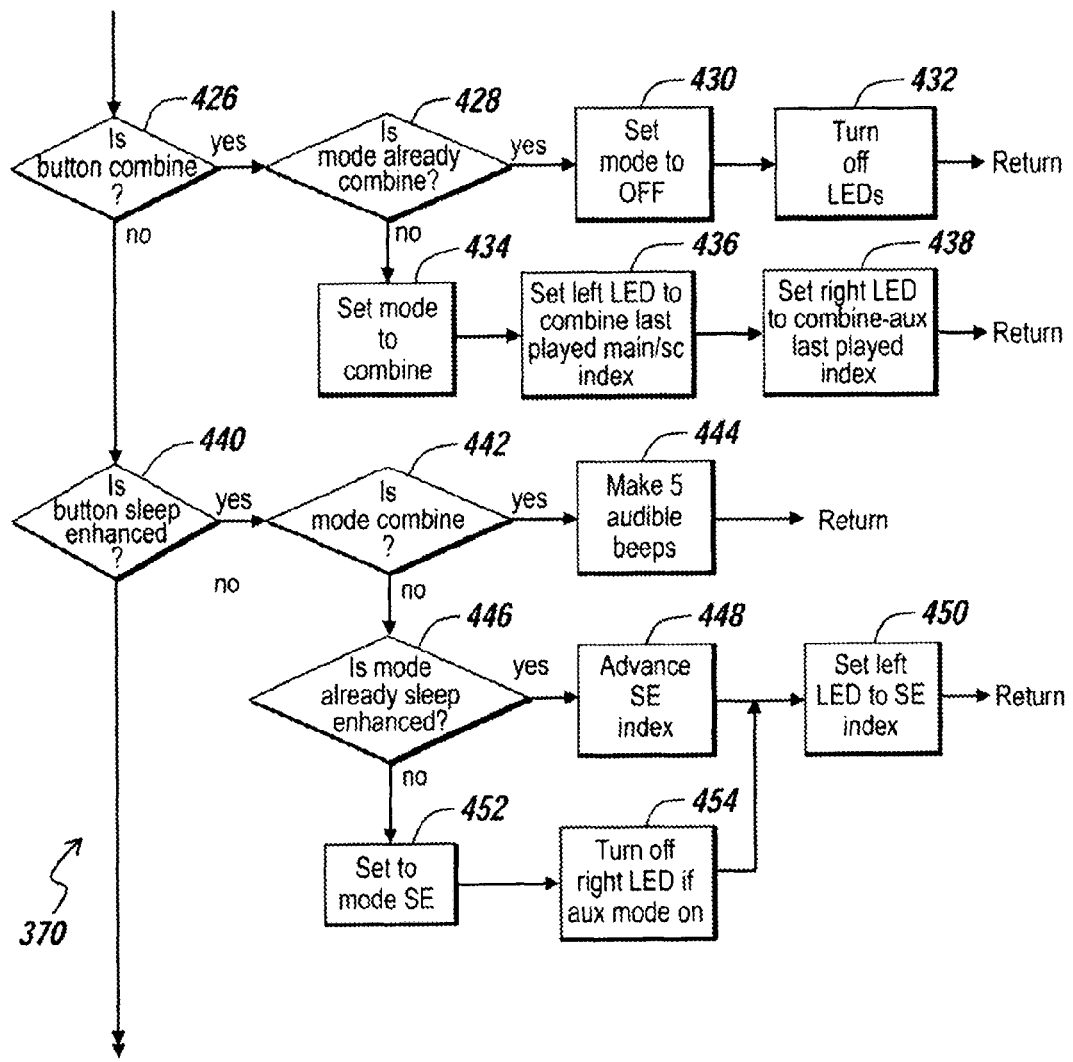
Figure 13:
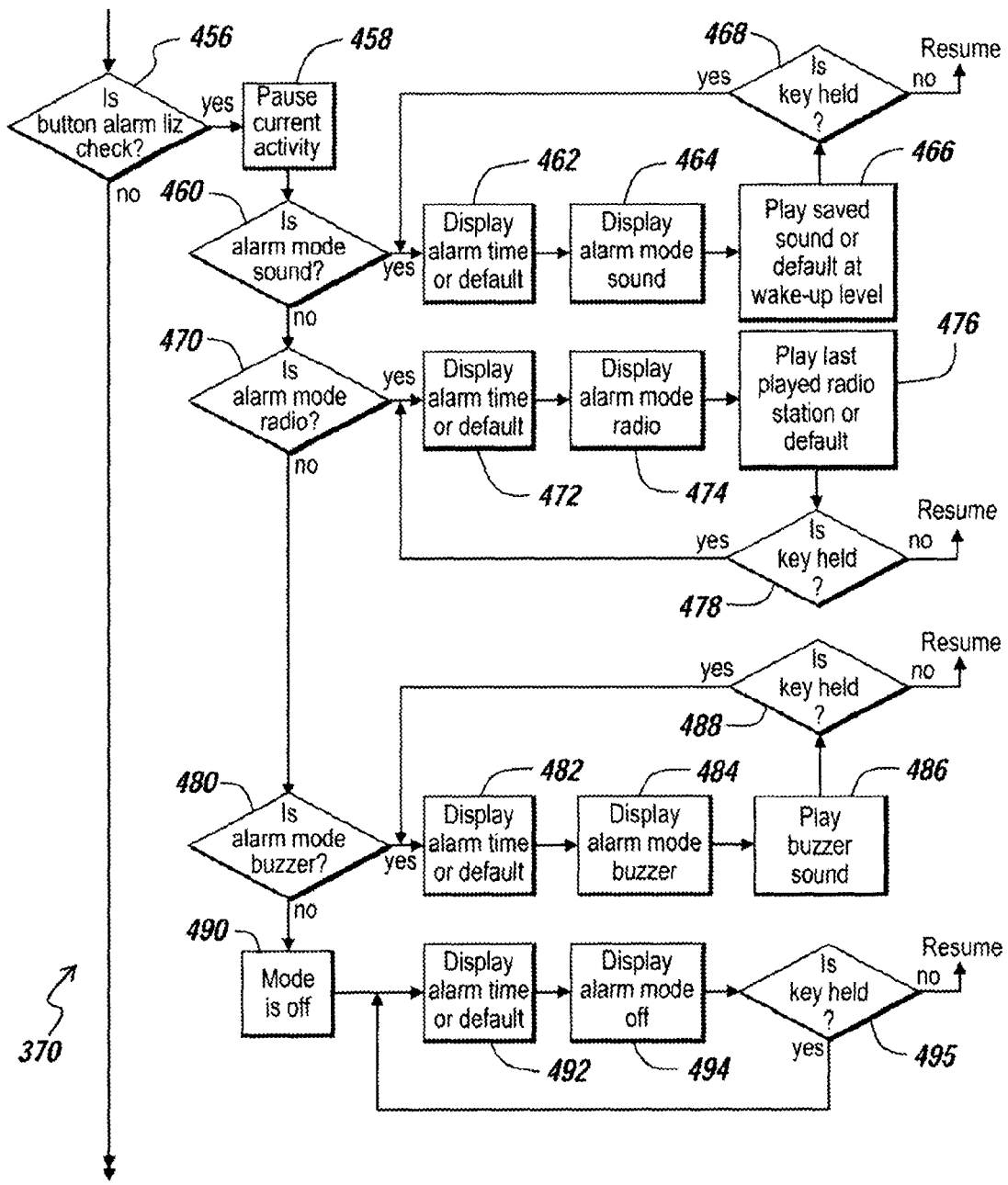
Figure 13:
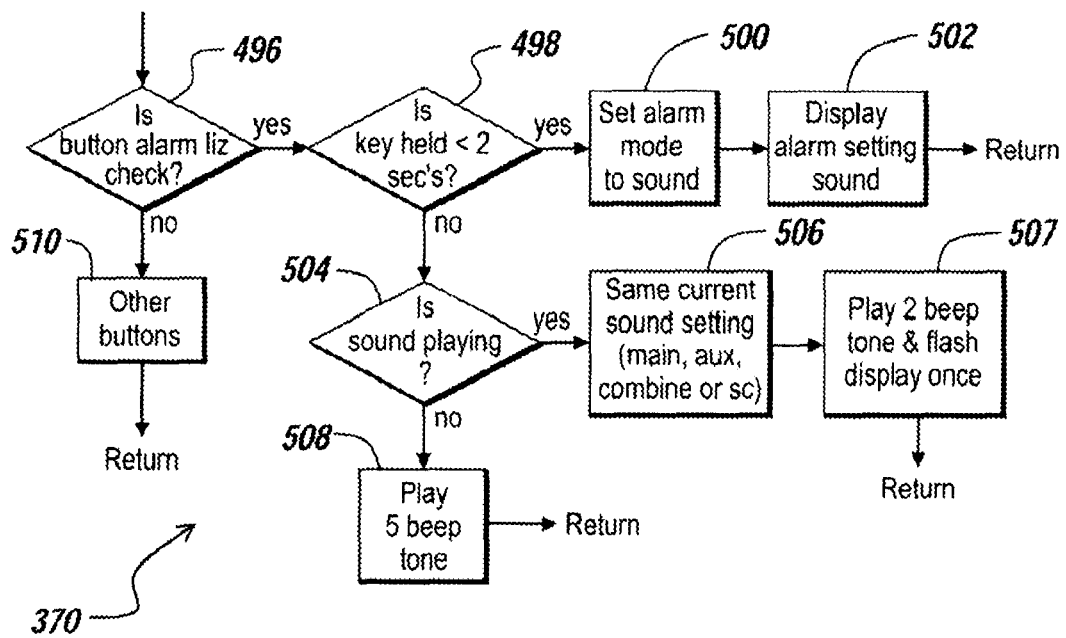

Referring now to FIG. 13, generally designated at 370 is a flow chart of an exemplary handle buttons subroutine of the digital sound relaxation and sleep-inducing system in accord with the present invention.

As shown by block 372, the processor is operative to determine if the button depressed is the main button.

As shown by block 374, if the mode is combine when the main button is depressed, the processor is operative to advance the combine main index as shown by block 376 and to set the LED of the left bank of LED's to the combine main index as shown by block 378. But if the mode is not combine and the mode is already main as shown by block 380, the processor is operative to advance the main index as shown by block 382 and to set the left LED to the main index as shown by block 384.

If the mode is not already main, the processor is operative to set the mode to main as shown by block 386, and to turn off any lighted LED of the right bank of LED's as shown by block 388.

As shown by block 390, the processor is next operative to determine if the button depressed is the sound card button.

As shown by block 392, if the mode is combine when the sound card button is depressed, the processor is operative to advance the combine sound card index as shown by block 394 and to set the LED of the left bank of LED's to the combine sound card index as shown by block 396. But if the mode is not and the mode is already sound card as shown by block 398, the processor is operative to advance the sound card index as shown by block 400 and to set the left LED to the sound card index as shown by block 402.

If the mode is not already sound card, the processor is operative to set the mode to sound card as shown by block 404, and to turn off any lighted LED of the right bank of LED's as shown by block 406.

As shown by block 408, if the button depressed is the auxiliary button, the processor is next operative to determine whether the mode is combine as shown by block 410. If it is, the processor is operative to advance the combine auxiliary index as shown by block 412, and to set the LED of the right bank of LED's to the combine auxiliary index as shown by the block 414.

As shown by block 416, if the mode is not combine and the mode is already auxiliary mode, the processor is operative to advance the auxiliary index as shown by block 418 and to set the right LED to the auxiliary index as shown by block 420.

But if the mode is not already auxiliary, the processor is operative to set the mode to auxiliary as shown by block 422, and to turn off the LED of the left bank of LED's as shown by block 424.

As shown by block 426, the processor is next operative to determine if the button depressed is the combine button. If the mode is combine when the combine button is depressed as shown by block 428, the processor is operative to set the mode to off mode as shown by block 430 and to turn off the LED's of the left and right banks of LED's as shown by block 432. If the mode is not combine when the combine button is depressed, the processor is operative to set the mode to combine as shown by block 434, to set the LED of the left bank of LED's to the last played combine main or sound card index as shown by block 436, and to set the LED of the right bank of LED's to the last played combine auxiliary index as shown by block 438.

As shown by block 440, the processor is next operative to determine whether the button depressed is the sleep-induce button. If the mode is combine when the sleep-induce button is depressed, the processor is operative to make five (5) audible beep sounds indicating an error as shown by blocks 442 and 444. But if the mode is not combine and the mode is sleep-induce when the sleep-induce button is depressed as shown by block 446, the processor is operative to advance the sleep-induce index as shown by block 448 and to set the LED of the left bank of LED's to the sleep-induce index as shown by block 450. If the mode is not sleep-induce when the sleep-induce button is depressed, the processor is operative to set the mode to sleep-induce as shown by block 452, and to turn off any LED, if lighted, of the right bank of LED's as shown by block 454.

As shown by block 456, the processor is next operative to determine whether the alarm "one" or alarm "two" check buttons have been depressed. If so, the processor is operative to pause current activity as shown by block 458, and the processor is then operative to determine whether the mode is sound as shown by block 460. If it is, the processor is operative to display the wake-up time (or default) and mode as shown by blocks 462, 464, and to play the alarm wake-up sound selected (or default) at wake-up level as shown by block 466. The processor is then operative to determine if the key is being held as shown by block 468. If it is, processing branches to the block 462.

The processor is then operative to determine whether the mode is radio as shown by block 470. If it is, the processor is operative to display the wake-up time and mode as shown by blocks 472, 474 and to play the radio station (or default station) selected at wake-up level as shown by block 476. The processor is then operative to determine if the key is being held as shown by block 478. If it is, processing branches to the block 472.

The processor is then operative to determine whether the mode is buzzer as shown by block 480. If it is, the processor is operative to display the wake-up time (or default) and mode as shown by blocks 482,484, and to play the buzzer sound selected at wake-up level as shown by block 486. The processor is then operative to determine if the key is being held as shown by block 488. If it is, processing branches to the block 482.

As shown by block 490, the mode is off if the mode is not sound, or radio or buzzer when an alarm check button is depressed. In that event, the processor is operative to display the alarm time last set (or a default alarm setting) as shown by block 492, and to display alarm mode off status as shown by block 494. The processor is then operative to determine if the key is being held as shown by block 495. If it is, processing branches to the block 492.

As shown by block 496, the processor is next operative to determine whether the button depressed is either the alarm "one" or "two" sound selector buttons. As shown by block 498, if the key is held for less than two (2) seconds, the processor is operative to set alarm mode to sound as shown by block 500 and to display sound mode as the alarm setting as shown by block 502. If the key is held for more than two (2) seconds and a sound is playing as shown by block 504, the processor is operative to save the current sound as the alarm wake-up sound as show by block 506, and to play a two (2) beep tone and to flash the display once as shown by block 507. As shown by block 508, if a sound is not being played when the key is held for more than two (2) seconds, the processor plays a five (5) beat error tone.

As shown by block 510, the processor is next operative to handle other buttons. The other buttons form no part of the present invention and are not further described herein.

Figure 15:
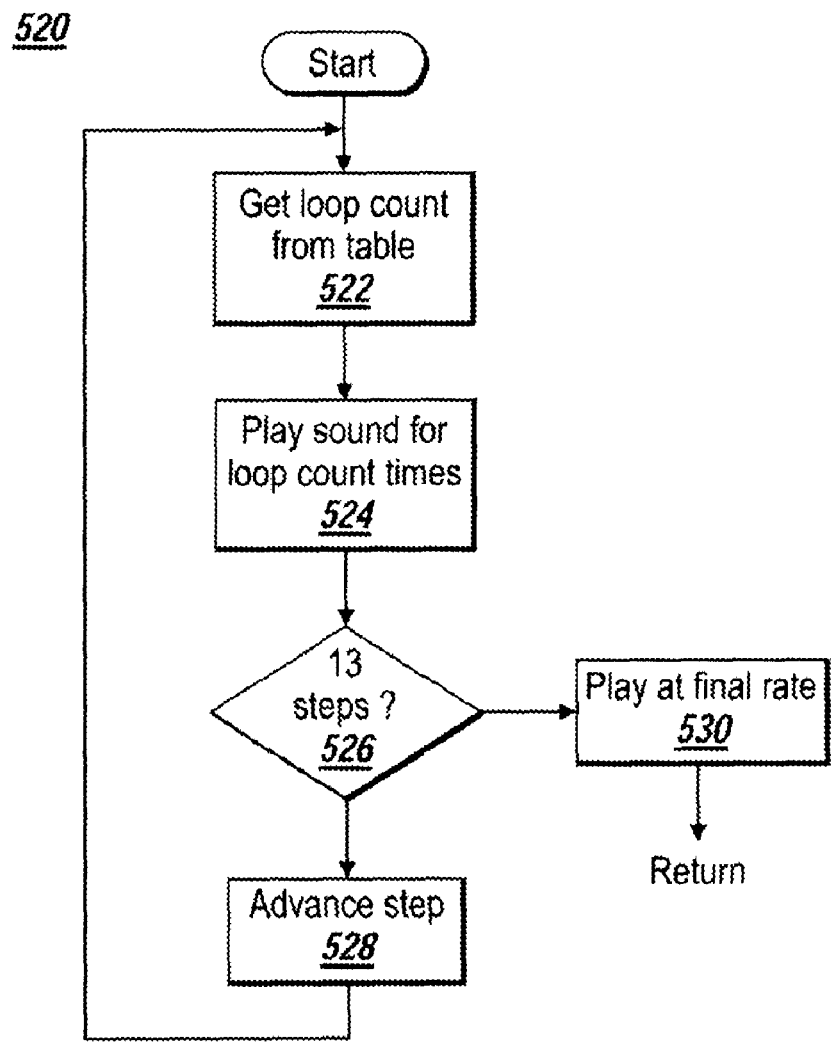
FIG. 15 is a flow chart illustrating an exemplary processor-implemented sleep-induce au a subroutine in accord with the present invention.

With reference to FIGS. 14 and 15, the sleep-induce sound replay of the digital sound relaxation and sleep-inducing system and method in accord with present invention will now be described. In the presently preferred embodiment, sleep-induce mode is implemented by playing the sample of any main sound selected by depression of the combination sleep-induce mode select and sleep-induce sequential sound selector switch. The sample of the prerecorded sound selected is replayed for a first predetermined time interval, preferably five (5) minutes, at the record (sampling) rate of the sample of the selected prerecorded sound stored in main memory. Thereafter, the sample of the prerecorded sound selected is replayed for a second time interval, preferably consisting of eleven (11) successive third intervals, each preferably of one (1) minute duration, at progressively slower play-back rates, whereafter, the sample of the prerecorded sound selected is replayed at a final play-back rate for the duration of replay. In the presently preferred embodiment, the sample of the prerecorded sound selected is replayed during the first time interval the whole number of times that the sample duration at the record rate is contained within the first time interval, and is replayed, during each successive third time interval, the whole number of times that the duration of the selected sample, factored by the ratio of the record and each another progressively slower play-back rate, is contained within each successive third time interval. FIG. 14 is a data table preferably stored in memory (main and/or sound card) that contains the whole number of times each sample is to be replayed during the first and third time intervals for the presently preferred Ocean Surf sound of duration 43.7 seconds; the Stream sound of 16.9 seconds duration; the Rain sound of 10.8 seconds duration; the White Noise sound of 11.0 seconds duration; the Woodlands sound of 45.4 seconds duration and Wind sound of 20.4 seconds duration; and for the presently preferred progressively slower play-back rates of 9260 Hz (the record or sampling rate of each sound) for the first time interval, and of 8929, 8620, 8333, 8065, 7692, 7463, 7143, 6849, 6579, 6250, and 5952 Hz for the eleven (11) successive third time intervals, and of the 5618 Hz final playback rate. As will be appreciated, the numbers to the right of the whole numbers, that give the actual number of times the sample duration is contained at the progressively slower play-back rates in the successive time intervals, as well as the sample names and durations, are not contained in the look-up table stored in memory, and any suitable rounding technique, other than that illustrated, may be employed.

Referring now to FIG. 15, generally designated at 520 is a flow chart of the sleep-induce play subroutine of the digital sound relaxation and sleep-inducing system and method in accord with the present invention. As shown by block 522, the processor is operative in sleep-induce replay mode to get loop count from the table stored in memory (main or sound card).

As shown by block 524, the processor is operative to play the sample of the prerecorded sound selected for the loop count number of times. The wait time is software controlled to achieve each preselected, progressively slower play-back frequency, although hardware-implemented, interrupt-driven or other techniques may be employed to implement the progressively slower play-back rates in successive time intervals.

As shown by block 526, the processor is then operative to determine whether the successive thirteen (13) steps of playback frequency of the presently preferred embodiment have been gone through. If not, the processor is operative to advance a step and change the wait time to decrement the playback frequency as shown by block 528; otherwise, the processor is operative to replay the sample of the prerecorded sound selected at the final replay rate as shown by block 530.

Many modifications of the presently disclosed invention will become apparent to those of skill in the art without departing from the inventive concepts. For example, other sleep-induce patterns and techniques, such as binaural holonomic integration and primordial subconscious processing, may be employed in accord with the present invention.

What is claimed is:

1. A digital sound machine for inducing sleep, comprising:
a housing; at least one speaker for reproducing sounds; a digital memory storing samples to be replayed of sounds previously recorded at a record rate that each contain start and end sounds that are acoustically seamless and that last a certain duration at said record rate;
at least one selector switch; and a processor-implemented sound controller mounted to said housing and connected to said digital memory, to said at least one selector switch and to said speaker and operative in sleep-induce mode, in response to user-input control selection entered via said at least one selector switch, (1) to replay the sound sample selected repetitively for a first time interval greater than the sample duration at the record rate the whole number of times that the sample duration is contained within the first time interval, and (2) to replay the sound sample for a second time interval that consists of a certain number of third time intervals during which, for every third time interval less than said second time interval, the sound sample is replayed at another, progressively slower rate the whole number of times that the selected sample duration, factored by the ratio of said record and each another, progressively slower rate, is contained within each said third time interval, wherein said certain number of third time intervals and each said another progressively slower rate are selected to replay the selected sound sample as to induce sleep as it is replayed at each progressively slower rate each said whole number of times the duration of the selected sound sample, factored by the ratio of said record and each another progressively slower rate, is contained in each said third time interval of said second interval.

2. A method of playing a prerecorded sound to induce such a deep relaxation state that helps a listener to fall asleep, comprising the steps of:
storing a sample to be replayed of a sound previously recorded at a record rate in digital memory of a sound conditioning machine in such a way that said sample contains start and end sounds that are acoustically seamless and lasts for certain duration at the record rate;

replaying the sound sample repetitively for a first time interval greater than the sample duration at the record rate the whole number of times that the sample duration is contained within the first time interval; and replaying the sound sample for a second time interval that consists of a certain number of third time intervals during which, for every third time interval less than said second time interval, the sound sample is replayed at another, progressively slower rate the whole number of times that the sample duration, factored by the ratio of said record and each another, progressively slower rate, is contained within each said third time interval, wherein said certain number of third time intervals and each said another progressively slower rate are selected to replay the selected sound sample as to induce sleep as it is replayed at each progressively slower rate each said whole number of times the duration of the selected sound sample, factored by the ratio of said record and each another progressively slower rate, is contained in each said third time interval of said second interval.

3. A digital sound machine for inducing sleep, comprising:
a housing; at least one speaker for reproducing sounds; at least one selector switch; at least one memory having digitally stored sounds selectable for replay; and a processor-implemented sound controller mounted to said housing and electrically connected to said at least one memory, said at least one speaker, and said at least one selector switch operative in one of a sound relaxation and noise masking mode=and a sleep-induce mode=such in response to user-input control selections entered via said at least one selector switch;

said processor-implemented sound controller is operative in said sound relaxation and noise masking mode (1) to retrieve from said memory a sound selected for replay and (2) to replay it continually and without disrupting pauses so as to induce relaxation and to mask noise;

said processor-implemented sound controller is operative in said sleep-induce mode (1) to retrieve from said memory a sound selected for replay, (2) to replay it continually and without disrupting pauses so as to induce relaxation and to mask noise for a first time interval, and (3) for a second time interval, (I) to select a slower replay rate, (ii) to replay said selected sound continuously and without disrupting pauses at said slower replay rate for a third time interval and (iii) to repeat steps (I) and (ii) for the duration of said second time interval so that the progressively slower sound replay and the listener's biorhythms synergistically co-act to induce such a state of deep relaxation that aids the listener to fall asleep; wherein each sound stored in said digital memory is a sample to be replayed of a sound previously recorded at a record rate: wherein each said sample contains start and end sounds that are acoustically seamless and lasts for a certain duration at said record rate; wherein said second time interval consists of a certain number of said third time intervals; wherein said processor-implemented sound controller in said sleep-induce mode (1) is operative to replay the selected sound sample repetitively for said first time interval greater than the sample duration at the record rate the whole number of times that the selected sample duration is contained within the first time interval, and (2) is operative to replay the sound sample for said second time interval that consists of said certain number of third time intervals during which, for every third time interval, the sound sample is replayed at another progressively slower rate the whole number of times that the sample duration, factored by the ratio of said record and each another progressively slower rate, is contained within each said third time interval, wherein said certain number of third time intervals and each said another progressively slower rate are selected to so replay the selected sound sample as to induce sleep as it is replayed at each progressively slower rate each said whole number of times the duration of the selected sound sample, factored by the ratio of said record and each another progressively slower rate, is contained in each said third time interval of said second interval.

\* \* \* \* \*